United States Patent [19]

Chu et al.

[11] Patent Number: 5,057,523

[45] Date of Patent: Oct. 15, 1991

[54] DIPEPTIDE QUINOLONE DERIVATIVES

[75] Inventors: Daniel T. Chu, Vernon Hills, Ill.; Robert Hallas, Kenosha, Wis.

[73] Assignee: Abbott Laboratories, Abbott Park, Ill.

[21] Appl. No.: 452,459

[22] Filed: Dec. 15, 1989

Related U.S. Application Data

[60] Division of Ser. No. 400,111, Sep. 1, 1989, which is a continuation-in-part of Ser. No. 328,401, Mar. 24, 1989, abandoned, which is a continuation-in-part of Ser. No. 313,260, Feb. 21, 1989, abandoned, which is a continuation-in-part of Ser. No. 247,990, Sep. 22, 1988, abandoned.

[51] Int. Cl.$^5$ ............................................. C07D 215/233
[52] U.S. Cl. ........................................ 514/312; 514/18; 514/300; 530/330; 530/331; 546/123; 546/156
[58] Field of Search ............... 514/312, 18; 546/156; 530/330, 331

[56] References Cited

U.S. PATENT DOCUMENTS

| | | | |
|---|---|---|---|
| 4,479,898 | 10/1984 | Gilvarg | 530/331 |
| 4,616,019 | 10/1986 | Chu | 546/123 |
| 4,621,088 | 11/1986 | Laruelle et al. | 546/123 |
| 4,649,144 | 3/1987 | Matsumoto et al. | 546/123 |
| 4,730,000 | 3/1988 | Chu | 546/156 |
| 4,735,949 | 4/1988 | Domagala et al. | 546/123 |
| 4,753,984 | 6/1988 | Delmotte | 530/330 |
| 4,851,418 | 7/1989 | Sanchez | 546/156 |
| 4,859,776 | 8/1989 | Chu et al. | 546/123 |
| 4,886,810 | 12/1989 | Matsumoto | 546/156 |
| 4,916,141 | 4/1990 | Sanchez | 546/123 |
| 4,920,120 | 4/1990 | Domagala et al. | 548/110 |
| 4,992,449 | 2/1991 | Bitha et al. | 514/312 |

OTHER PUBLICATIONS

Egawa et al., J. Med. Chem. 27, No. 12, pp. 543-548 (1984).

*Primary Examiner*—Donald G. Daus
*Attorney, Agent, or Firm*—Jerry F. Janssen; Andreas M. Danckers

[57] ABSTRACT

7-(3-A-amino-1-pyrrolidinyl) substituted naphthyridine and quinoline compounds wherein A is a solubilizing group selected from an amino acid residue or polypeptide chain.

7 Claims, No Drawings

DIPEPTIDE QUINOLONE DERIVATIVES

This application is a divisional of copending U.S. patent application, Ser. No. 400,111 filed Sept. 1, 1989 which is a continuation-in-part of copending U.S. patent application, Ser. No. 328,401, filed Mar. 24, 1989, now abandoned, which is a continuation-in-part of copending U.S. patent application, Ser. No. 313,260, now abandoned, filed Feb. 21, 1989, which is a continuation-in-part of copending U.S. patent application, Ser. No. 247,990, filed Sept. 22, 1988, now abandoned.

TECHNICAL FIELD

This invention relates to novel derivatives of naphthyridine and quinoline compounds, pharmaceutical compositions and their use as antibacterial agents in humans and mammals in need of such treatment. These compounds also have very low solubility at physiological pH which reduces their oral absorption.

BACKGROUND OF THE INVENTION

Quinoline and naphthyridine antibacterial compounds are well known in the art. For example, Chu, U.S. Pat. No. 4,730,000, issued Mar. 8, 1988 describes quinoline compounds with a 7 pyrrolidine substituent group having antibacterial properties, Chu, U.S. Pat. No. 4,616,019, issued Oct. 7, 1986 describes naphthyridine compounds with a 7-pyrrolidine substituent group with antibacterial properties. Matsumoto et al., U.S. Pat. No. 4,649,144, issued Mar. 10, 1988 describes 1,8-naphthyridine compounds with a 7 pyrrolidine substituent group with antibacterial activity, and Domagala et al., U.S. Pat. No. 4,735,949, issued Apr. 5, 1988 describes disubstituted 7-pyrrolidine-naphthyridine compounds with antibacterial activity. These compounds, however, have limited aqueous solubility which impairs their use in injectable formulations for intravenous, intramuscular or subcutaneous application. These compounds also have very low solubility at physiological pH which reduces their oral absorption.

In order to improve the solubility of various compounds for pharmaceutical use, their structure has been modified. For example, Gilvarg et al., U.S. Pat. No. 4,479,898, issued Oct. 30, 1984 describes peptide chains substituted by a nucleophilic residue in the alpha position for use as prodrugs to increase cell membrane permeability and Delmotte et al., U.S. Pat. No. 4,753,984, issued June 28, 1988 describes water soluble macromolecular prodrugs in which a polyhydroxylated polyamine is linked to a therapeutically active drug by a peptide chain.

SUMMARY OF THE INVENTION

The present invention relates to compounds having enhanced aqueous solubility.

More particularly, this invention relates to new quinolines and naphthyridines where the 7-pyrrolidine ring is 3-A-amino substituted, wherein A is a solubilizing group. The solubilizing group is an amino acid residue or a polypeptide chain, preferably a di-, tri- or tetrapeptide. These novel compounds are useful as broad spectrum antibacterial agents, with activity against both gram positive and gram negative bacteria, as well as enterobacteria.

More particularly, this invention relates to compounds of the following formula:

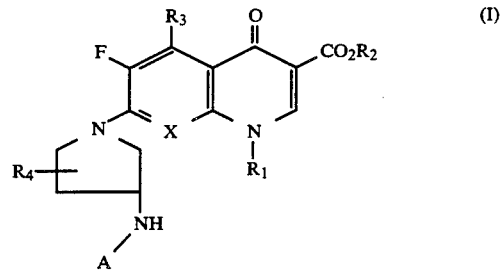

wherein
$R_1$ is alkyl, haloalkyl, hydroxyalkyl, cycloalkyl, vinyl, aryl or aryl substituted with one to three substituents independently selected from the group consisting of hydrogen, halogen, alkyl, haloalkyl, alkanoyloxy, and a group having the formula —Y—$R_5$, wherein Y is O or S and $R_5$ is hydrogen or alkyl;
$R_2$ is hydrogen, alkyl, haloalkyl or a carboxy protecting group;
$R_3$ is hydrogen or $NH_2$;
X is N, CH, COH, C—O—alkyl, CF, CCl, C-alkyl or C-NH-alkyl;
$R_4$ is hydrogen, alkyl or haloalkyl; and
A is a solubilizing group; and the pharmaceutically acceptable salts thereof.

The present invention includes antibacterial compositions comprising an antibacterially effective amount of a compound of Formula I and a pharmaceutically acceptable carrier or diluent.

The present invention also includes a method for treating bacterial infections in a mammal in need of such treatment which comprises administering to the mammal an effective amount of a compound of Formula I.

DETAILED DESCRIPTION OF THE INVENTION

This invention relates to compounds of the following formula:

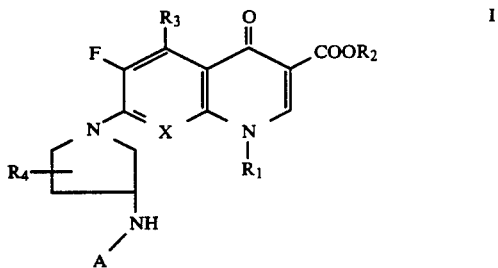

wherein
$R_1$ is a member selected from the group consisting of alkyl, haloalkyl, hydroxyalkyl, cycloalkyl, vinyl, aryl and aryl substituted with one to three substituents independently selected from the group consisting of hydrogen, halogen, alkyl, halosubstituted alkyl, alkanoyloxy, a group having the formula —Y—$R_5$, wherein Y is O or S and $R_5$ is hydrogen or alkyl;
$R_2$ is hydrogen, alkyl, haloalkyl or a carboxy protecting group;
$R_3$ is hydrogen or $NH_2$;
X is N, CH, COH, C—O—alkyl, CF, CCl, C—alkyl or C—NH—alkyl;

$R_4$ is hydrogen, alkyl and haloalkyl; and

A is a solubilizing group; and the pharmaceutically acceptable salts thereof.

This invention also relates to antibacterial compositions comprising an antibacterially effective amount of a compound of Formula I and a pharmaceutically acceptable carrier or diluent.

This invention also relates to a method for treating bacterial infections in a mammal in need of such treatment by administering to the mammal an effective amount of a compound of Formula I.

A preferred group are compounds of the formula:

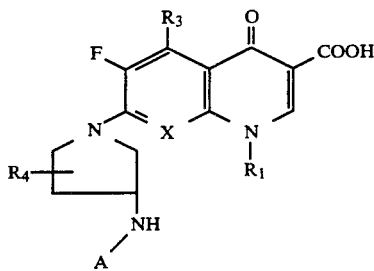

wherein $R_1$ is ethyl, 2-fluoroethyl, t-butyl, cyclopropyl, 4-fluorophenyl, or 2,4-difluorophenyl;

$R_3$ is hydrogen or $NH_2$;

X is N, CH, CF, $CCH_3$ or CCl;

$R_4$ is hydrogen, alkyl or haloalkyl;

A is an amino acid residue or a polypeptide chain, and the pharmaceutically acceptable salts thereof.

A more preferred group of compounds of this invention are compounds of the above formula wherein A is Gly-Phe, Phe, NorVal (hereinafter Nval), Ala-Phe, Gly-Nval, Ala-Nval, Gly-Ala, Leu-Nval, Ala-Met, Ala-Leu, Leu-Leu, Leu-Met, Leu-Ala, Met-Leu, Met-Ala, D-Ala-L-Ala, Phe-Ala, Val-Ala, Val-Leu, Gly-Gly, Gly-Gly-Nval, Met-Nval, Nval-Gly, Nval-Ala, Gly-Gly-Gly, Gly-Gly-Ala, Gly-Nval-Nval, Gly-Ala-Ala, Gly-Gly-Gly-Gly, Gly-Gly-Gly-Ala, Gly-Gly-Gly-Nval, Ala-Phe-Gly, Gly-Phe-Ala, Nval-Nval, Gly, Phe-Gly, Val, Ala-Ala, Ala, Leu, Met, Pro, Lys, Asn, Asp and Methionine-sulfone (hereinafter Met(sulfone)).

Compounds that are representative of the preferred class of compounds of this invention include the following compounds and their hydrochloride salts:

1. 7-(3-Gly-Phe-amino-1-pyrrolidinyl)-6-fluoro-1-(4-fluorophenyl)-1,4,-dihydro-4-oxo-quinoline-3-carboxylic acid
2. 7-(3-Gly-Phe-amino-1-pyrrolidinyl)-6-fluoro-1-(2,4-difluorophenyl)-1,4,-dihydro-4-oxo quinoline-3-carboxylic acid
3. 7-(3-Ala-amino-1-pyrrolidinyl)-6-fluoro 1-(4-fluorophenyl)-1,4,-dihydro-4-oxo-quinoline-3-carboxylic acid
4. 7-(3-Ala-amino-1-pyrrolidinyl)-6-fluoro-1-(2,4-difluorophenyl)-1,4,-dihydro-4-oxo-quinoline-3-carboxylic acid
5. 7-(3-Nval-amino-1-pyrrolidinyl)-6-fluoro-1-(4-fluorophenyl)-1,4-dihydro-4-oxo-quinoline-3-carboxylic acid
6. 7-(3-Nval-amino-1-pyrrolidinyl)-6-fluoro-1-(2,4difluorophenyl)-1,4,-dihydro-4-oxo-quinoline-3-carboxylic acid
7. 7-(3-Nval-Nval-amino-1-pyrrolidinyl)-6-fluoro-1-(2,4-difluorophenyl)-1,4,-dihydro-4-oxo-quinoline-3-carboxylic acid.
8. 7-(3-Nval-Nval-amino-1-pyrrolidinyl)-6-fluoro-1-(4-fluorophenyl)-1,4,-dihydro-4-oxo-quinoline-3-carboxylic acid
9. 7-(3-Gly-amino-1-pyrrolidinyl)-6-fluoro-1-(4-fluorophenyl)-1,4,-dihydro-4-oxo quinoline 3carboxylic acid
10. 7-(3-Gly-amino-1-pyrrolidinyl)-6-fluoro-1-(2,4-difluorophenyl)-1,4,-dihydro-4-oxo-quinoline-3-carboxylic acid
11. 7-(3-Phe-Gly-amino-1-pyrrolidinyl)-6-fluoro-1-(4-fluorophenyl)-1,4,-dihydro-4-oxo-quinoline-3-carboxylic acid
12. 7-(3-Val-amino-1-pyrrolidinyl)-6-fluoro-1-(2,4-difluorophenyl)-1,4,-dihydro-4-oxo-quinoline-3-carboxylic acid
13. 7-(3-Asn-amino-1-pyrrolidinyl)-6-fluoro-1-(2,4-difluorophenyl)-1,4-dihydro-4-oxo-quinoline-3--carboxylic acid
14. 7-(3-Ala-Phe-Gly-amino-1-pyrrolidinyl)-6-fluoro-1-(4-fluorophenyl)-1,4,-dihydro-4-oxo-quinoline-3-carboxylic acid
15. 7-(3-Gly-Phe-Ala-amino-1-pyrrolidinyl)-6-fluoro-1-(2,4-difluorophenyl)-1,4,-dihydro-4-oxo-quinoline-3-carboxylic acid
16. 7-(3-Ala-Phe-amino-1-pyrrolidinyl)-6-fluoro-1-(2,4-difluorophenyl)-1,4,-dihydro-4-oxo quinoline-3-carboxylic acid
17. 7-(3-Ala-Phe-amino-1-pyrrolidinyl)-6-fluoro 1-(4-fluorophenyl)-1,4, -dihydro-4-oxo-quinoline-3-carboxylic acid
18. 7-(3-Leu-amino-1-pyrrolidinyl)-6-fluoro-1-(2,4-difluorophenyl)-1,4,-dihydro-4-oxo-quinoline-3-carboxylic acid
19. 7-(3-Leu-amino-1-pyrrolidinyl)-6-fluoro-1-(4-fluorophenyl)-1,4,-dihydro-4-oxo-quinoline-3-carboxylic acid
20. 7-(3-Ala-Ala-amino-1-pyrrolidinyl)-6-fluoro-1-(4-fluorophenyl)-1,4,-dihydro-4-oxo-quinoline-3-carboxylic acid
21. 7-(3-Ala-Ala-amino-1-pyrrolidinyl)-6-fluoro-1-(2,4-difluorophenyl)-1,4,-dihydro-4-oxo-quinoline-3-carboxylic acid
22. 7-(3-Gly-Phe-amino-1-pyrrolidinyl)-6-fluoro-1-(4-fluorophenyl)-1,4,-dihydro-4-oxo-1,8-naphthyridine-3-carboxylic acid
23. 7-(3-Gly-Phe-amino-1-pyrrolidinyl)-6-fluoro-1-(2,4-difluorophenyl)-1,4,-dihydro-4-oxo-1,8-naphthyridine-3-carboxylic acid
24. 7-(3-Pro-amino-1-pyrrolidinyl)-6-fluoro-1-(2,4-difluorophenyl)-1,4-dihydro-4-oxo-1,8-naphthyridine-3-carboxylic acid
25. 7-(3-Lys-amino-1-pyrrolidinyl)-6-fluoro-1-(2,4-difluorophenyl)-1,4-dihydro-4-oxo-1,8-naphthyridine-3-carboxylic acid
26. 7-(3-Phe-amino-1-pyrrolidinyl)-6-fluoro-1-(2,4-difluorophenyl)-1,4-dihydro-4-oxo-1,8-naphthyridine-3-carboxylic acid
27. 7-(3-Phe-amino-1-pyrrolidinyl)-6-fluoro-1-(4-fluorophenyl)-1,4,-dihydro-4-oxo 1,8 naphthyridine-3-carboxylic acid
28. 7-(3-Nval-amino-1-pyrrolidinyl)-6-fluoro-1-(2,4-difluorophenyl)-1,4-dihydro-4-oxo-1,8-naphthyridine-3-carboxylic acid 29. 7-(3-Nval-amino-1-pyrrolidinyl)-6-fluoro-1-(4-fluorophenyl)-1,4,-dihydro-4-oxo-1,8-naphthyridine-3-carboxylic acid
30. 7-(3-Nval-Nval-amino-1-pyrrolidinyl)-6-fluoro-1-(4-fluorophenyl)-1,4,-dihydro-4-oxo-1,8-naphthyridine-3-carboxylic acid
31. 7-(3-Nval-Nval-amino-1-pyrrolidinyl)-6-fluoro-1(2,4-difluorophenyl)-1,4,-dihydro-4-oxo-1,8-naphthyridine-3-carboxylic acid
32. 7-(3-Gly-amino-1-pyrrolidinyl)-6-fluoro-1-(2,4-difluorophenyl)-1,4,-dihydro-4-oxo-1,8-naphthyridine-3-carboxylic acid
33. 7-(3-Gly-amino-l-pyrrolidinyl)-6-fluoro-1-(4-fluorophenyl)-1,4,-dihydro-4-oxo-1,8-naphthyridine-3-carboxylic acid
34. 7-(2-methyl-4-Nval-amino-1-pyrrolidinyl)-6-fluoro-1-(2,4-difluorophenyl)-1,4,-dihydro-4-oxo-1,8-naphthyridine-3-carboxylic acid
35. 7-(2-methyl-4-Nval-amino-1-pyrrolidinyl)-6-fluoro-1-cyclopropyl-1,4-dihydro-4-oxo-1,8-naphthyridine-3-carboxylic acid
36. 7-(2-methyl-4-Nval-amino-1-pyrrolidinyl)-6,8-difluoro-1-cyclopropyl-1,4-dihydro-4-oxo-quinoline-3-carboxylic acid
37. 7-(2-methyl-4-Nval-amino-1-pyrrolidinyl)-6-fluoro-1-cyclopropyl-1,4-dihydro-4-oxo quinoline-3-carboxylic acid
38. 7-(3-Met-amino-1-pyrrolidinyl)-6-fluoro-1-(2,4-difluorophenyl)-1,4,-dihydro-4-oxo-1,8-naphthyridine-3-carboxylic acid
39. 7-(3-Met(sulfone)-amino-1-pyrrolidinyl)-6-fluoro-1-(2,4-difluorophenyl)-1,4-dihydro-4-oxo-1,8-naphthyridine-3-carboxylic acid
40. 7-(3-Val-amino-1-pyrrolidinyl)-6-fluoro-1-(2,4-difluorophenyl)-1,4,-dihydro-4-oxo-1,8-naphthyridine-3-carboxylic acid
41. 7-(3-Asn-amino-1-pyrrolidinyl)-6-fluoro-1-(2,4-difluorophenyl)-1,4-dihydro-4-oxo-1,8-naphthyridine-3-carboxylic acid
42. 7-(3-Ala-Phe-Gly-amino-1-pyrrolidinyl)-6-fluoro-1-(2,4-difluorophenyl)-1 4,-dihydro-4-oxo-1,8-naphthyridine-3-carboxylic acid
43. 7-(3-Gly-Gly-Nval-amino-1-pyrrolidinyl)-6-fluoro-1-(2,4-difluorophenyl)-1,4-dihydro-4-oxo-1,8-naphthyridine-3-carboxylic acid
44. 7-(3-Gly-Phe-Ala-amino-1-pyrrolidinyl)-6-fluoro-1-(4-fluorophenyl)-1.4,-dihydro-4-oxo-1,8-naphthyridine-3-carboxylic acid
45. 7-(3-Asp-amino-1-pyrrolidinyl)-6-fluoro-1-(2,4-difluorophenyl)-1,4-dihydro-4-oxo-1,8-naphthyridine-3-carboxylic acid
46. 7-(3-Ala-Phe-amino-1-pyrrolidinyl)-6-fluoro-1-(2,4-difluorophenyl)-1,4,-dihydro-4-oxo-1,8-naphthyridine-3-carboxylic acid
47. 7-(3-Ala-Phe-amino-1-pyrrolidinyl)-6-fluoro-1-(4-fluorophenyl)-1,4,-dihydro-4-oxo-1,8-naphthyridine-3-carboxylic acid
48. 8-(3-Leu-amino-1-pyrrolidinyl)-6-fluoro-1-(4-fluorophenyl)-b 1,4,-dihydro-4-oxo-1,8-naphthyridine-3-carboxylic acid
49. 7-(3-Leu-amino-1-pyrrolidinyl)-6-fluoro-1-(2,4-difluorophenyl)-1,4-dihydro-4-oxo-1,8-naphthyridine-carboxylic acid
50. 7-(3-Nval-amino-1-pyrrolidinyl)-6-fluoro-1-ethyl-1,4-dihydro-4-oxo-1,8-naphthyridine-3-carboxylic acid
51. 7-(3-Nval-amino-1-pyrrolidinyl) 6-fluoro 1-ethyl-1,4-dihydro-4-oxo-quinoline-3-carboxylic acid
52. 7-(3-Nval-amino-1-pyrrolidinyl)-8-difluoro-1-t-butyl-1,4-dihydro-4-oxo-quinoline-3-carboxylic acid
53. 7-(3-Ala-Ala-amino-1-pyrrolidinyl)-6-fluoro-1-(4-fluorophenyl)-1,4,-dihydro-4-oxo-1,8-naphthyridine-3-carboxylic acid
54. 7-(3-Ala-Ala-amino-1-pyrrolidinyl)-6-fluoro-1-(2,4-difluorophenyl)-1,4,-dihydro-4-oxo-1,8-naphthyridine-3-carboxylic acid
55. 7-(3-Gly-Phe-amino-1-pyrrolidinyl) 6-fluoro-1-cyclopropyl-1,4-dihydro-4-oxo-quinoline-3-carboxylic acid
56. 7-(3-Phe-amino-1-pyrrolidinyl)-6-fluoro-1-cyclopropyl-1,4-dihydro-4-oxo-quinoline-3-carboxylic acid
57. 7-(3-Nval-amino-1-pyrrolidinyl)-6-fluoro-1-cyclopropyl-1,4-dihydro-4-oxo-quinoline-3-carboxylic acid
58. 7-(3-Nval-Nval-amino-1-pyrrolidinyl)-6-fluoro-1-cyclopropyl-1,4-dihydro-4-oxo-quinoline-3-carboxylic acid
59. 7-(3-Leu-amino-1-pyrrolidinyl)-6-fluoro-1-cyclopropyl-1,4-dihydro-4-oxo-quinoline-3-carboxylic acid
60. 7-(3-Val-amino-1-pyrrolidinyl)-6-fluoro-1-cyclopropyl-1,4-dihydro-4-oxo-quinoline-3-carboxylic acid
61. 7-(3. Met-amino-1-pyrrolidinyl)-6-fluoro-1-cyclopropyl-1,4-dihydro-4-oxo-quinoline-3-carboxylic acid
62. 7-(3-Met(sulfone)-amino-1-pyrrolidinyl)-6-fluoro 1-cyclopropyl-1,4 dihydro 4 oxo quinoline-3 carboxylic acid
63. 7-(3-Phe-amino-1-pyrrolidinyl)-6-fluoro-8-chloro-1-cyclopropyl-1,4-dihydro-4-oxo-quinoline-3-carboxylic acid
64. 7-(3-Ala-amino-1-pyrrolidinyl)-6-fluoro-1-t--butyl-1,4-dihydro-4-oxo-quinoline-3-carboxylic acid
65. 7-(3-Ala-amino-1-pyrrolidinyl)-6-fluoro-1-t-butyl-1,4-dihydro-4-oxo-1,8-naphthyridine-3-carboxylic acid
66. 7-(3-Nval-amino-1-pyrrolidinyl)-6-fluoro-8-chloro-1-cyclopropyl-1,4-dihydro-4-oxo-quinoline-3/carboxylic acid
67. 7-(3-Leu-amino-1-pyrrolidinyl)-6-fluoro-8-chloro-1-cyclopropyl-1,4-dihydro-4-oxo-quinoline-3-carboxylic acid
68. 7-(3-Val-amino-1-pyrrolidinyl)-6-fluoro-8-chloro-1-cyclopropyl-1,4-dihydro-4-oxo-quinoline-3-carboxylic acid
69. 7-(3-Nval-amino-1-pyrrolidinyl)-6-fluoro-8-chloro 1-cyclopropy-1,4-dihydro-4-oxo-quinoline-3-carboxylic acid
70. 7-(3-Leu-amino-1-pyrrolidinyl)-6-fluoro-1-cyclopropyl-1,4-dihydro-4-oxo-1,8-naphthyridine-3-carboxylic acid
71. 7-(3-Nval-amino-1-pyrrolidinyl)-6-fluoro-1-cyclopropyl-1,4-dihydro-4-oxo-1,8-naphthyridine-3-carboxylic acid
72. 7-(3-Val-amino-1-pyrrolidinyl)-6-fluoro-1-cyclopropyl-1,4-dihydro-4-oxo-1,8-naphthyridine-3-carboxylic acid
73. 7-(3-Gly-Phe-amino-1-pyrrolidinyl)-6-fluoro-1-cyclopropyl-1,4-dihydro-4-oxo-1,8-naphthyridine-3-carboxylic acid
74. 7-(3-Leu-amino-1-pyrrolidinyl)-5-amino-6,8-difluoro-1-cyclopropyl-1,4-dihydro-4-oxo-quinoline-3-carboxylic acid
75. 7-(3-Nval-amino-1-pyrrolidinyl)-6-fluoro-1-t-butyl 1,4 dihydro 4 oxo quinoline-3-carboxylic acid 76. 7-(3-Nval-amino-1-pyrrolidinyl)-6-fluoro-1-t-butyl-1,4-dihydro-4-oxo-1,8-naphthyridine-3-carboxylic acid
77. 7-(3-Nval-amino-1-pyrrolidinyl)-5-amino-6,8-difluoro-1-cyclopropyl-1,4-dihydro-4-oxo-quinoline-3-carboxylic acid
78. 7-(3-Ala-amino-1-pyrrolidinyl)-5-amino-6,8-difluoro-1-cyclopropyl-1,4-dihydro-4-oxo-quinoline-3-carboxylic acid
79. 7-(3-Val-amino-1-pyrrolidinyl)-5-amino-6,8-difluoro-1-cyclopropyl-1,4-dihydro-4-oxo-quinoline-3-carboxylic acid
80. 7(3-Asn-amino-1-pyrrolidinyl)-6,8-difluoro-1-cyclopropyl-1,4-dihydro-4-oxo-quinoline-3-carboxylic acid
81. 7-(3-Leu-amino-1-pyrrolidinyl)-6,8-difluoro-1-cyclopropyl-1,4-dihydro-4-oxo-quinoline-3-carboxylic acid
82. 7-(3-Ala-amino-1-pyrrolidinyl)-6,8-difluoro-1-cyclopropyl-1,4-dihydro-4-oxo-quinoline-3-carboxylic acid
83. 7-(3-Nval-amino-1-pyrrolidinyl)-6,8-difluoro-1-cyclopropyl-1,4-dihydro-4-oxo-quinoline-3-carboxylic acid
84. 7-(3-Nval-amino-1-pyrrolidinyl)-6-fluoro-8-methyl-1-cyclopropyl-1,4-dihydro-4-oxo-quinoline-3-carboxylic acid
85. 7-(3-Ala-Nval-amino-1-pyrrolidinyl)-6-fluoro-1-(2,4-difluorophenyl)-1,4-dihydro-4-oxo-1,8-naphthyridine-3-carboxylic acid
86. 7-(3-Leu-Nval-amino-1-pyrrolidinyl)-6-fluoro-1-(2,4-difluorophenyl)-1,4-dihydro-4-oxo-1,8-naphthyridine-3-carboxylic acid
87. 7-(3-Met-Nval-amino-1-pyrrolidinyl)-6-fluoro-1-(2,4-difluorophenyl)-1,4-dihydro-4-oxo 1,8-naphthyridine-3-carboxylic acid
88. 7-(3-Gly-Gly-amino-1-pyrrolidinyl)-6-fluoro-1-(2,4-difluorophenyl)-1,4-dihydro-4-oxo-1,8-naphthyridine-3-carboxylic acid
89. 7-(3-Gly-Nval-amino-1-pyrrolidinyl)-6-fluoro-1-(2,4-difluorophenyl)-1,4-dihydro-4-oxo-1,8-naphthyridine-3-carboxylic acid
90. 7-(3-Nval-Gly-amino-1-pyrrolidinyl)-6-fluoro-1-(2,4-difluorophenyl)-1,4-dihydro-4-oxo-1,8-naphthyridine-3-carboxylic acid
91. 7-(3-Nval-Ala-amino-1-pyrrolidinyl)-6-fluoro1-(2,4-difluorophenyl)-1,4-dihydro-4-oxo-1,8-naphthyridine-3-carboxylic acid
92. 7-(3-Gly-Gly-Gly-amino-1-pyrrolidinyl)-6-fluoro-1-(2,4-difluorophenyl)-1,4-dihydro-4-oxo-1,8-naphthyridine-3-carboxylic acid
93. 7-(3-Gly-Nval-Nval-amino-1-pyrrolidinyl)-6-fluoro-1-(2,4-difluorophenyl)-1,4-dihydro-4-oxo-1,8-naphthyridine 3-carboxylic acid
94. 7-Gly-Gly-Ala-amino-1-pyrrolidinyl)-6-fluoro-1-(2,4-difluorophenyl)-1,4-dihydro-4-oxo-1,8-naphthyridine-3-carboxylic acid
95. 7-(3-Gly-Ala-Ala-amino-1-pyrrolidinyl)-6-fluoro-1-(2,4-difluorophenyl)-1,4-dihydro-4-oxo-1,8-naphthyridine-3-carboxylic acid
96. 7-(3-Gly-Gly-Gly-Gly-amino-1-pyrrolidinyl)-6-fluoro-1-(2,4-difluorophenyl)-1,4-dihydro-4-oxo-1,8-naphthyridine-3-carboxylic acid
97. 7-(3-Gly-Gly-Gly-Ala-amino-1-pyrrolidinyl)-6-fluoro-1-(2,4-difluorophenyl)-1,4-dihydro-4-oxo-1,8-naphthyridine-3-carboxylic acid
98. 7-(3-Gly-Gly-Gly-Nval-amino-1-pyrrolidinyl)-6-fluoro-1-(2,4-difluorophenyl)-1,4-dihydro-4-oxo-1,8-naphthyridine-3-carboxylic acid
99. 7-(3-Gly-Gly-amino-1-pyrrolidinyl)-6-fluoro-1-cyclopropyl-1,4-dihydro-4-oxo-1,8-naphthyridine-3-carboxylic acid
100. 7-(3-Nval-Nval-amino-1-pyrrolidinyl)-6-fluoro-1-cyclopropyl-1,4-dihydro-4-oxo-1,8-naphthyridine-3-carboxylic acid
101. 7-(3-Gly-Gly-Gly-amino-1-pyrrolidinyl)-6-fluoro-1-chloro 1-cyclopropyl 1,4 dihydro 4-oxo-1,8-naphthyridine-3-carboxylic acid
102. 7-(3-Gly-Gly-amino-1-pyrrolidinyl)-6-fluoro-1-cyclopropyl-1,4-dihydro-4-oxo-quinoline-3-(carboxylic acid
103. 7-(3-Nval-Nval-amino-1-pyrrolidinyl)-6-fluoro-1-cyclopropyl-1,4-dihydro-4-oxo-quinoline-3-carboxylic acid
104. 7-(3-Gly-Gly-Gly-amino-1-pyrrolidinyl)-6-fluoro-1-cyclopropyl-1,4-dihydro-4-oxo-quinoline-3-carboxylic acid
105. 7-(3-Gly-Nval-amino-1-pyrrolidinyl)-6-fluoro 1-cyclopropyl-1,4-dihydro-4-oxo-quinoline-3-carboxylic acid
106. 7-(3-Gly-Nval-amino-1-pyrrolidinyl)-6-fluoro 1-cyclopropyl-1,4-dihydro-4-oxo-1,8-naphthyridine-3-carboxylic acid
107. 7-(3-Gly-Ala-amino-1-pyrrolidinyl)-6-fluoro-1-(2,4-difluorophenyl)-1,4-dihydro-4-oxo-1,8-naphthyridine-3-carboxylic acid
108. 7-(3-Ala-Met-amino-1-pyrrolidinyl)-6-fluoro 1-(2,4-difluorophenyl)-1,4-dihydro-4-oxo-1,8-naphthyridine-3-carboxylic acid;
109. 7-(3-Met-Met-amino-1-pyrrolidinyl)-6-fluoro-1-(2,4-difluorophenyl)-1,4-dihydro-4-oxo-1,8;-naphthyridine-3-carboxylic acid;
110. 7-(3-Leu-Met-amino-1-pyrrolidinyl)-6-fluoro-1-(2,4-difluorophenyl)-1,4-dihydro-4-oxo-1,8-naphthyridine-3-carboxylic acid;
111. 7-(3-Leu-Leu-amino-1-pyrrolidinyl)-6-fluoro-1-(2,4-difluorophenyl)-1,4-dihydro-4-oxo-1,8-naphthyridine-3-carboxylic acid;
112. 7-(3-Ala-Leu-amino-1-pyrrolidinyl)-6-fluoro-1-(2,4-difluorophenyl)-1,4-dihydro-4-oxo-1,8-naphthyridine-3-carboxylic acid;
113. 7-(3-Met-Leu-amino-1-pyrrolidinyl)-6-fluoro 1-(2,4-difluorophenyl)-1,4-dihydro-4-oxo-1,8-naphthyridine-3-carboxylic acid;
114. 7-(3-Phe-Ala-amino-1-pyrrolidinyl)-6-fluoro-1-(2,4-difluorcphenyl)-1,4-dihydro-4-oxo-1,8-naphthyridine-3-carboxylic acid;
115. 7-(3-Leu-Ala-amino-1-pyrrolidinyl)-6-fluoro-1-(2,4 difluorophenyl)-1,4-dihydro-4-oxo-1,8-naphthyridine-3-carboxylic acid;
116. 7-(3-Met-Ala-amino-1-pyrrolidinyl)-6-fluoro-1-(2,4-difluorophenyl)-1,4-dihydro-4-oxo-1,8-naphthyridine-3-carboxylic acid;
117. 7-(3-Val-Ala-amino-1-pyrrolidinyl)-6-fluoro-1-(2,4-difluorophenyl)-1,4-dihydro-4-oxo 1,8-naphthyridine-3-carboxylic acid;
118. 7-(3-Val-Leu-amino-1-pyrrolidinyl)-6-fluoro-1-(2,4-difluorophenyl)-1,4-dihydro-4-oxo-1,8-naphthyridine-3-carboxylic acid; and
119. 7-(3-D-Ala-L-Ala-Amino-1-pyrrolidinyl)-6-fluoro-1-(2,4-difluorophenyl)-1,4-dihydro-4-oxo-1,8-naphthyridine-3-carboxylic acid.

As used herein, the term "carboxy-protecting group" refers to a carboxy group which has been esterified with one of the commonly used carboxylic acid protecting ester groups employed to block or protect the carboxylic acid functionality. In addition, compounds containing a carboxy protecting group can be used as prodrugs whereby the carboxy protecting group can be hydrolyzed enzymatically to release the biologically active parent acid. Such protected carboxy groups are noted for their ease of cleavage by hydrolytic methods to the corresponding carboxylic acid. Further, such carboxyprotecting groups can be cleaved to yield the corresponding free carboxy group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. Representative protecting groups include $C_1$ to $C_8$ alkyl (e.g., methyl, ethyl, tertiary butyl,) benzyl and substituted derivatives thereof such as alkoxy and nitrobenzyl groups, dialkylaminoalkyl (e.g. dimethylaminoethyl), acyloxyalkyl groups such as pivaloyloxymethyl and propionyloxy methyl.

As used herein, the term "pharmaceutically acceptable salts" refers to non toxic acid addition salts and alkaline earth metal salts of the compounds of Formula I. The salts can be prepared in situ during the final isolation and purification of the compounds of Formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate glucoheptonate, lactobionate, lauryl sulphate salts and the like. Representative alkali or alkaline earth metal salts include the sodium, calcium, potassium and magnesium salts, and the like.

As used herein, the term "halogen" or "halo" refers to chloro, bromo, fluoro and iodo groups.

As used herein, the term "alkyl" includes both straight or branched chain radicals of one to six carbon atoms. Representative of such radicals are methyl, ethyl, propyl, iso-propyl, t-butyl, sec-butyl, isobutyl, amyl, butyl, neopentyl, hexyl and the like.

As used herein, the term "cycloalkyl" refers to those rings having three to six carbon atoms such as cyclopropyl, cyclobutyl, cyclopentyl and cyclohexyl.

As used herein, the term "haloalkyl", refers to halogen substituted straight and branched carbon chain radicals of one to six carbon atom and one to three halogen atoms. Representative of such groups are fluoromethyl, 2-fluoroethyl, 2-chloroethyl, 2,2-dichloroethyl, 2-chloropropyl, 2-chloroisopropyl, 3-iodobutyl, and the like.

As used herein, the term "hydroxyalkyl" refers to -OH appended to an alkyl radical.

As used herein, the term "alkanoyloxy" refers to $R_6COO$ wherein $R_6$ is alkyl.

As used herein, the term "aryl" refers to aromatic radical having five to six atoms in the ring system and may contain one to three hetero atoms selected from S, O and N, the remaining atoms being carbon atoms. Representative aromatic radicals include phenyl, pyridyl, pyrazinyl, thiazoyl, furyl and thienyl.

As used herein, the term "solubilizing group" refers to an amino acid residue or a poly peptide chain containing two to four, or more amino acid residues which are joined covalently through peptide bonds. The amino acid residues of the invention encompass the 20 naturally occurring, standard amino acids, (as designated by their three letter symbols); 4-hydroxyproline, hydroxylysine, demosine, isodemosine, 3-methylhistidine, norvaline (Nval), beta-alanine, gama amino butyric acid, homocysteine, homoserine, citrulline, ornithine and methionine sulfone.

For the sake of convenience and understanding, the amino acids three letter and single letter designations are as follows:

|  | 3- or 4-letter | 1-letter |
| --- | --- | --- |
| Alanine | Ala | A |
| Arginine | Arg | R |
| Asparagine | Asn | N |
| Aspartic Acid | Asp | D |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Norvaline | Nval | — |
| Phenylalanine | Phe | F |
| Proline | Pro | P |
| Serine | Ser | S |
| Threonine | Thr | T |
| Tryptophan | Try | O |
| Tyrosine | Tyr | Y |
| Valine | Val | V |

The preferred amino acid residues are those with a non polar group such as Ala, Val, Nval, Leu, Met, Gly, Pro, Phe; or a basic polar group, such as Lys.

For purposes of clarity, it should be noted that the 3-amino function of the 7-pyrrolidinyl group forms a bond with the carboxyl group of an alpha amino acid residue and, in turn, if a polypeptide is desired, the amino acid residues are bonded to each other via conventional peptide bonding; ie., the alpha amino group of the first linked amino acid residue is bonded to the carboxyl group of the second alpha amino acid residue, etc.

As used herein, the term "amino protecting group" refers to a group which protects the N-terminal of the amino acid residue. The alpha amino group of each amino acid employed in the peptide synthesis must be protected during the coupling reaction to prevent side reactions involving the reactive alpha-amino function. It should also be recognized that certain amino acids contain reactive side-chain functional groups (e.g. sulfhydryl, epsilon-amino, carboxyl, and hydroxyl), and that such functional groups must also be protected both during the initial and subsequent coupling steps. Suitable protecting groups are known in the art See for example *Protective Groups in Organic Chemistry*, M. McOmie, Editor, Plenum Press, N. Y., 1973.

In selecting a particular protecting group, certain conditions must be observed. An alpha-amino protecting group (1) must be stable, (2) must render the alpha amino function inert under the conditions employed in the coupling reaction, and (3) must be readily removable after the coupling reaction under conditions that will not remove side chain protecting groups and will not alter the structure of the peptide fragment. A side chain protecting group (1) must render the side chain functional group inert under the conditions employed in the coupling reaction, (2) must be stable under the conditions employed in removing the alpha amino protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity and affect the selection of the agents employed for their removal. For example, certain protecting groups, such as triphenylmethyl and 2-(p-biphenylyl)isopropyloxycarbonyl are very labile and can be cleaved under mild acid conditions. Other protecting groups such as t-butyloxycarbonyl, t-amyloxycarbonyl, adamantyl-oxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl, halo-benzyloxycarbonyl, p-nitrobenzyloxycarbonyl, cyclo-alkyloxycarbonyl, and isopropyloxycarbonyl, are even less labile and require strong acids, such as hydrogen fluoride, hydrogen bromide, or boron trifluoroacetate in trifluoroacetic acid for their removal.

Illustrative examples of amino acid protecting groups are set forth below.

A. for an alpha amino group, protecting groups may include (a) acyl type groups, such as formyl, trifluoracetyl, phthalyl, p-toluenesulfonyl (tosyl), benzenesulfonyl, nitrophenylsulfenyl, and the like; (b) aromatic urethane type groups, such as benzyloxycarbonyl and substituted benzyloxycarbonyl, such as, for example, p-chlorobenzyloxycarbonyl, p-bromobenzyloxycarbonyl, p-nitrobenzyloxycarbonyl and p-methoxybenzyloxycarbonyl, o-chlorobenzyloxy-carbonyl, 2,4-dichlorobenzyloxycarbonyl, 2,6-dichlorobenzyloxycarbonyl, and the like; (c) aliphatic urethane type groups such as t-butyloxycarbonyl, t-amyloxycarbonyl, isopropyloxycarbonyl, 2-(p-biphenylyl)-isopropyloxycarbonyl, allyloxycarbonyl, and the like; (d) cycloalkyl urethane groups such as cyclopentyloxycarbonyl, cyclohexyloxycarbonyl, cyclo-heptyloxycarbonyl, adamantyloxycarbonyl, and the like; (e) thiourethane type groups such as phenylthio-carbonyl; (f) alkyl type groups such as triphenylmethyl, and (g) trialkylsilane groups, such as trimethylsilane. A preferred a amino protecting group is t-butyloxycarbonyl (BOC).

B. For the epsilon-amino protecting group present in lysine, protection may be by any of the groups mentioned hereinabove for protection of an alpha-amino group. Typical groups include, for example, benzyloxycarbonyl, p-chlorobenzyloxycarbonyl, p-bromobenzyloxycarbonyl, o-chlorobenzyloxy-carbonyl, 2,6-dichlorobenzyloxycarbonyl, 2,4-dichlorobenzyloxycarbonyl, o-bromobenzyloxycarbonyl, p-nitro-benzyloxycarbonyl t-butyloxycarbonyl, isopropyloxy carbonyl, t-amyloxycarbonyl, cyclopentyloxycarbonyl, cyclohexyloxycarbonyl, cycloheptyloxycarbonyl, adamantyloxycarbonyl, p-toluenesulfonyl, and the like. The preferred epsilon amino protecting group is o-chlorobenzyloxycarbonyl (ClBzl).

C. For the hydroxy group of serine, threonine, or tyrosine, protection may be, for example, by $C_1$–$C_4$ alkyl, such as methyl, ethyl, and t-butyl; benzyl; substituted benzyl, such as p-methoxybenzyl, p-nitrobenzyl, p-chlorobenzyl, and o-chlorobenzyl; $C_1$–$C_3$ alkanoyl, such as formyl, acetyl, and propionyl; triphenylmethyl; or benzoyl. The preferred hydroxyl protecting group is benzyl (Bzl).

D. For the carboxyl group of aspartic acid or glutamic acid, protection may be, for example, by esterification using groups such as benzyl, t-butyl, cyclohexyl, cyclopentyl, and the like. The current groups of choice are cyclohexyl and cyclopentyl.

As used herein the term "C or carboxy terminal activating group" refers to a group which renders the carboxyl group of an amino acid residue more susceptible to reaction with a free N-terminal amino group (of a peptide fragment).

For example, the amino acid can be converted to a mixed anhydride by reaction of a protected amino acid with ethyl chloroformate, phenyl chloroformate, sec-butyl chloroformate, isobutyl chloroformate, pivaloyl chloride, or like acid chlorides. Alternatively, the amino acid can be converted to an active ester such as a 2,4,5-trichlorophenyl ester, a pentachlorophenyl ester, a p-nitrophenyl ester, an ester formed from N-hydroxysuccinimide, N-hydroxyphthalimide, or an ester formed from 1-hydroxybenzotriazole.

As used herein, the terms "aralkyloxy-carbonyl", "alkyloxycarbonyl and "cyclooxycarbonyl" refer to the amino protecting groups as noted above, wherein the aryl, alkyl and cycloalkyl radicals are as defined herein.

Certain substituents on the pyrrolidine ring may exist in the cis or trans stereochemical forms. The pure isomers or mixtures thereof are also contemplated by the invention.

Certain compounds of the invention may exist in optically active forms. The pure R isomers, pure S isomers as well as mixtures thereof, including the racemic mixtures are contemplated by the invention. Additional asymmetric carbon atoms may be present in a substituent such as an alkyl group. All such isomers as well as mixtures thereof are intended to be included in the invention.

The stereoisometric configuration of the amino acids of the invention may be either the D- or L-form, or a mixture of configurations. Preferably, however, the amino acids are all of the L-form. The sequence of amino acids in a peptide chain read from left to right, from the amino (N) terminal to the carboxy (C)-terminal as are conventionally used in the art.

The compounds according to the invention exhibit a broad antibacterial spectrum against Gram-positive and Gram negative germs.

The compounds of the invention are also useful as chemotherapeutic active compounds for the treatment of mammals.

In addition, the compounds may be used in scrub solutions for surface inhibition of bacterial growth, e.g., on counter surfaces, and the like, and as substances for preserving inorganic and organic materials, in particular all kinds of organic materials, for example, polymers, lubricants, paints, fibers, leather, paper and wood, foodstuffs and water.

The compounds according to the invention are particularly active against bacteria and bacteria-like micro organisms. They are therefore particularly suitable in human and veterinary medicine for the prophylaxis an chemotherapy of local and systemic infections carried by pathogems such as Staphylococci (Staph. aureus and Staph. epidermidis) and Streptococci (Strep. agalactiae, Strept. facealis, Strep. pneumoniae, Strep. bovis and Strept. pyogenes); Neisseria, (Neisseria gonorrhoeme)

Enterobacteriaceae, for example Escherichia, Haemophilus influenza, Citrobacter (Citrob freundil and Citrob. divermis), Salmonella and Shigella and Klebeiellae (Klebs, pneumoniae and Klebs. oxyvocs), Micrococcus, Entrobacter (Ent. aerogenes and Ent. agglumerenx), Hafnia, Serratia (Serr. marcescens), Proteus (*Pr mirabillis, Pr. rettgerri* and *Pr. vulgaris*), Providencia, Yersinia and the genus Acinetobacter. The antibacterial spectrum also includes the genus Pseudomonas (Ps. aeruginosa, Ps. cepacia and Ps. maltophilia) the genus Chlamydia (such as *Chlamydia trachomatis*) as well as anaerobic bacteria, such as, for example, *bacteroides fragilis*, representatives of the genus Peptococcus, Peptostreptococcus and the genus Clostridium; and furthermore Mycoplasma (*M. pneumoniae, M. hominis* and *M. urealyticum*) and Mycobactria, for example Mycobacterium tuberculosis.

Examples of diseases which can be caused by the pathogens (or mixed infections as noted above) and can be treated by compounds of this inventions are: infectious diseases in humans, such as, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, abscesses of the liver, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral region, infections following dental operations, osteomyelitis, septic arthritis, chlocystitis, peritonitis with appendicitis, chlolangitis, intraabdominal abscesses, pancreatitis, sinusitis, mastoiditis, mastitis, tonsillitis, typhoid fever, meningitis and infections of the nervous system, salpingitis, endometritis, genital infections, pelveoperitonitis and eye infections.

Representative examples of animals and infections in such animals which may be treated are: pigs: coli diarrhea, enterotoxaemia, sepsis, dysentery, salmonellosia, metritis mastitisagalactiae syndrome and mastitis; ruminants (cattle, sheep, goats): diarrhea, sepsis, bronchopneumonia, salmonellosis, pasteurellosis, mycoplasmosis and genital infections; horses: bronchopneumonia, joint ill, puerperal and postpuerperal infections and salmonellosis; dogs and cats: bronchopneumonia, diarrhea, dermatitis, otitis, urinary tract infections and prostatitis; poultry (chicken, turkeys, guail, pigeons, ornamental birds and others): mycoplasmosis, E. coli infections, chronic infections of the respiratory tract, salmonellosis, pasteurellosis and psittacosis.

Bacterial infections in the breeding and rearing of stock and ornamental fish can likewise be treated, the antibacterial spectrum being increased beyond the above mentioned pathogens to further pathogens, such as, for example, Pasteurella, Brucella, Campylobacter, Listeris, Erysipelothrix, Corynebactria, Borellia, Treponema, Nocardia, Rickettsia and Yersinia.

In addition to exhibiting highly effective antibacterial activity, the compounds of the invention exhibit increased and improved solubility characteristics as compared with known naphthyridine and quinoline 3 carboxylic acid compounds. Also, it is believed that the compounds of the invention may act as prodrugs of known naphthyridine and quinoline-3 carboxylic acid compounds such as tosufloxacin.

The present invention includes one or more of the compounds of Formula I formulated into compositions together with one or more non-toxic pharmaceutically acceptable carriers adjuvants or vehicles which are collectively referred to herein as carriers, for parenteral injection, for oral administration in solid or liquid form, for rectal administration, and the like.

Non-toxic, inert pharmaceutically suitable carriers include solid, semi solid or liquid diluents, fillers and formulation auxiliaries of all types.

The compositions can be administered to humans and animals either orally, rectally, parenterally (intravenously, intramuscularly or subcutaneously), intracisternally, intravaginally, intraperitoneally or locally (powders, ointments or drops), and for the therapy of infections in hollow cavities and body cavities.

Compositions according to the invention for parenteral injection may comprise pharmaceutically acceptable sterile aqueous or nonaqueous solutions, dispersions, suspensions or emulsions and sterile powders for reconstitution into sterile injectible solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various anti-bacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers and extenders, as for example, starches, lactose, sucrose, glucose, mannitol and silicic acid, (b) binders, as for example, carboxymethylcellulose, alginates, gelatin and polyvinylpyrrolidone, sucrose and acacia,(c) humectants, for example glycerol, (d) disintegrating agents, as for example, agar agar, calcium carbonate, potato or tapioca starch, alginic acid, certain complex silicates, and sodium carbonate (e) solution retarders, as for example paraffin, and (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof.

In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

The solid dosage forms of tablets, dragees, capsules, pills and granules can be prepared with coatings and shells, such as enteric coatings and others well known in this art. They may optionally contain opacifying agents, and can also be of such composition that they release the active compound or compounds only or preferentially in a certain part of the intestinal tract, optionally in a delayed manner, examples of embedding compositions which can be used are polymeric substances and waxes.

The active compounds can also be in micro-encapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerolformal, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxy-ethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administrtion of a compound of this invention include ointments, pastes, creams, gels, powders, sprays and inhalants. The active component is admixed under sterile conditions with a pharmaceutically acceptable carrier and any needed preservatives or buffers as may be required. Opthalmological formulations, ear drops, eye ointments, powders and solutions are also contemplated as being within the scope of this invention.

The ointments, pastes, creams and gels may contain, in addition to an active compound of this invention, excipients such as animal and vegetable fats, waxes, paraffins, starch, tragacanth, cellulose derivatives, polyethylene glycols, silicones, bentonites, silicic acid, talc and zinc oxide, or mixtures thereof.

Powders and sprays can contain, in addition to compounds of this invention, excipients such as lactose, talc, silicic acid, aluminum hydroxide, calcium silicates and polyamide powder, or mixtures of these substances. Sprays can additionally contain customary propellants, as for example, chlorofluoro-hydrocarbons.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I are about 0.1 to about 750, preferably about 0.25 to about 500 and most preferably about 0.5 to about 300 mg. of active ingredient per kg. of body weight and are effective when administered to a mammalian patient suffering from an infection caused by a susceptible organism. If desired, the daily dose may be divided into multiple doses for administration, e.g., two to four times per day.

An individual unit dose preferably contains the active compound or compounds according to this invention in amounts of about 0.5 to about 80, in particular 0.5 to 30 mg/kg of body weight. It may, however, be necessary to deviate from the dosages mentioned.

Synthesis of the Compounds

The naphthyridine antibacterial compounds of this invention having a 7-((3-amino)-1-pyrrolidinyl) substituent group can be synthesized by conventional means known in this art as for example, those described in U.S. Pat. No. 4,616,019, issued Oct. 7, 1986 or U.S. Pat. No. 4,649,144, issued Mar. 10, 1987, whose disclosures are incorporated herein by reference.

The quinoline antibacterial compounds of this invention having a 7-(3-amino-1-pyrrolidinyl) substituent group are also prepared by conventional means known in this art as for example, those described in U.S. Pat. No. 4,730,000, issued Mar. 8, 1988 and U.S. Pat. No. 4,735,949, issued Apr. 5, 1988, whose disclosures are incorporated herein by reference.

A general reaction scheme for preparation of the compounds of this invention by standard amino acid coupling techniques as well known in the art and exemplified by Example 1-3 is as follows:

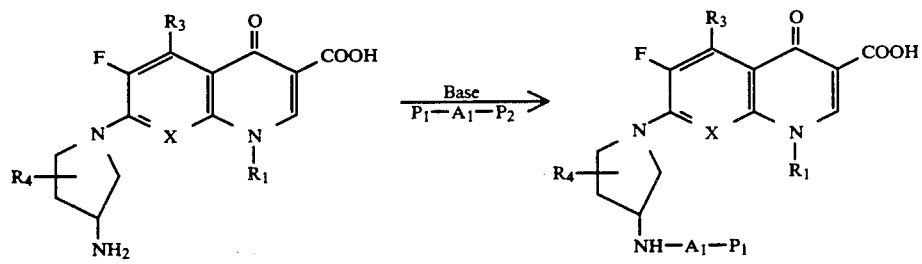

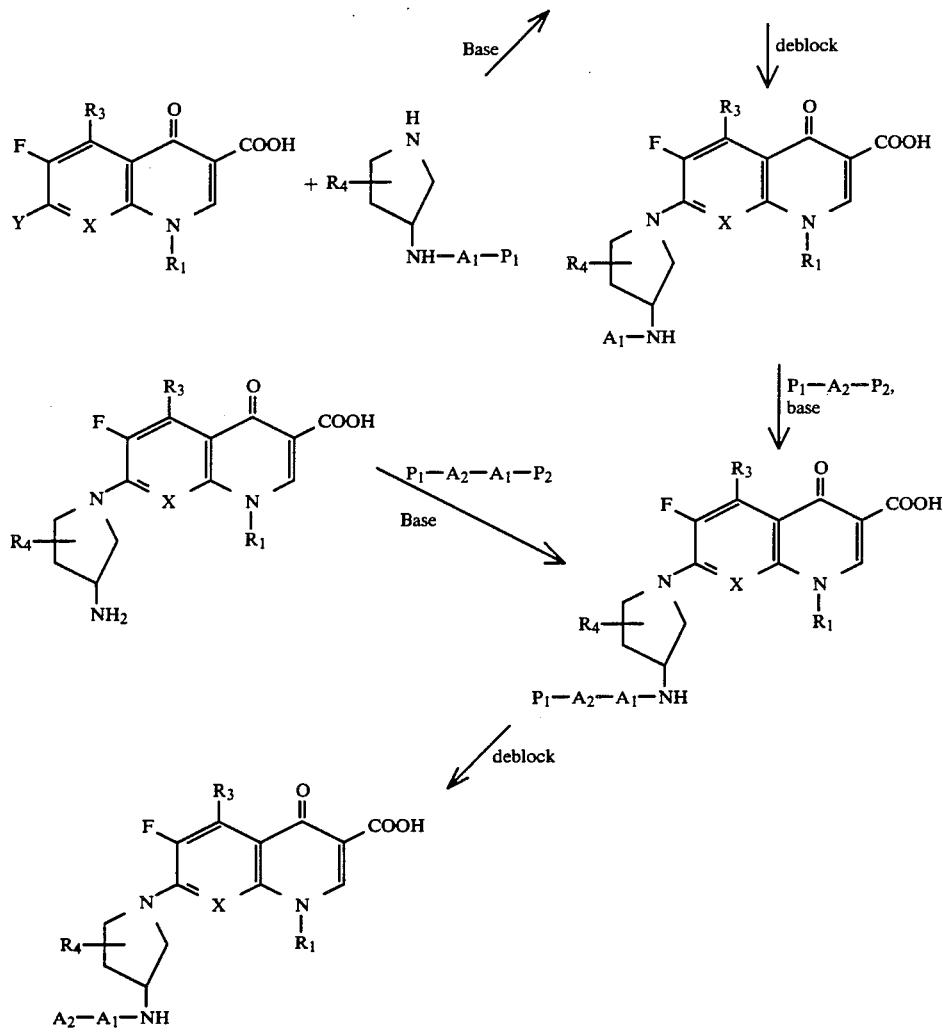

wherein X, $R_1$, and $R_3$ and $R_4$ are as defined previously; $A_1$ and $A_2$ are amino acid residues as described previously, and $P_1$ is an amino protecting and $P_2$ a carboxy activating group, as also described previously and Y is a leaving group such as chloro or bromo or fluoro or thiomethyl group.

The peptide solubilizing groups of this invention can be prepared by any of a variety of recognized peptide synthesis techniques including classical (solution) methods, solid phase methods, and the more recently available recombinant DNA methods.

One method of preparation of the peptide solubilizing groups of this invention is by the solid phase technique in which the amino acid sequence is constructed sequentially from an initial insoluble resin-supported C terminal amino acid. Techniques for the solid phase method are described by J. Stewart et al., *Solid Phase Peptide Synthesis*, Freeman and Co., San Francisco, 1969.

In general, in the solid phase method, the amino acid corresponding to the C-terminal amino acid residue of the desired peptide is anchored to an insoluble resin support, and the peptide chain then is formed beginning at the resin-supported C-terminal amino acid. Individual amino acids are introduced sequentially until the desired amino acid sequence is obtained. Alternatively, small peptide fragments can be prepared and introduced into the peptide chain in the desired order. The peptide chain remains attached to the resin throughout synthesis, and, upon completion of the chain, the peptide is cleaved from the resin.

The peptide chain is attached to the polystyrene resin by means of an ester linkage formed between the carboxyl group of the C-terminal moiety and one of the methylene groups present on the resin matrix as sites for such attachment. The polystyrene resin is a styrene polymer which is cross linked by the addition of about 0.5 to about 3% divinylbenzene and which is chloromethylated or hydroxymethylated to provide sites for ester formation. An example of a hydroxymethylated resin is described by Bodanszky et al., Chem. Ind. (London), 38, 1597-98 (1966). A chloromethylated polystyrene resin is commercially available from Lab System, Inc., San Mateo, California. The resin is also described by Stewart et al., *Solid Phase Peptide Synthesis*, Freeman and Co., San Francisco, Calif., pp. 1–6.

The amino acids are coupled using techniques well known in the art for the formation of peptide bonds. One method involves converting the amino acid to a derivative that will render the carboxyl terminus group more susceptible to reaction with the free N-terminal amino group of the peptide fragment.

Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. See Schroder and Lubke, The Peptides, Academic Press, 1965, Chapter III.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid hydrogen fluoride. This reagent not only will cleave the peptide from the resin but will also remove all protecting and activating groups. Hence, use of this reagent will directly afford the desired peptide.

When it is desired to cleave the peptide without removing protecting groups, the protected peptide-resin can undergo methanolysis to give the protected peptide in which the C terminal carboxyl group is methylated. The methyl ester can then be hydrolyzed under mild, alkaline conditions to give the free C-terminal carboxylic acid. The protecting groups on the peptide chain then can be removed by treatment with a strong acid, such as liquid hydrogen fluoride. A particularly useful technique for methanolysis is that of G. Moore et al., Peptides, Proc. 5th Amer. Pept. Symp., M. Goodman and J. Meinhofer, Eds., John Wiley, N.Y., 1977, pp. 518–521, in which the protected peptide resin is treated with methanol and potassium cyanide in the presence of crown ether.

Another method for cleaving the protected peptide from the resin is by ammonolysis or by treatment with hydrazine. The resulting C-terminal amide or hydrazide can be hydrolyzed to the free C-terminal carboxyl, and the protecting groups can be removed conventionally.

It will also be recognized that the protecting groups present on the N terminal a-amino group may be removed preferentially either before or after the protected peptide is cleaved from the resin support.

The protecting groups are otherwise removed by appropriate treatment as known in the art. Removal of the dinitrophenyl group from His-containing peptides is usually carried out with N-methylmercaptoacetamide in DMF. The N-formyl group is usually removed from Try by treatment with NaOH at pH 11.5 in the presence of hydrazine. Other protecting groups are removed by treatment with anisole and anhydrous HF.

The following non limiting examples illustrate a preferred method for preparing representative compounds of the invention.

EXAMPLE 1

7-[(3-Gly-L-Phe-amino)-1-pyrrolidinyl]-1-(2, 4-difluorophenyl)-6-fluoro-1,4-dihydro-4-oxo-1,8-naphthyridine-3-carboxylic acid hydrochloride.

a) To a cold solution of 7-(3-amino-1-pyrrolidinyl)-1-(2,4-difluorophenyl)-1,4 dihydro-4-oxo-1,8-naphthyridine-3-carboxylic acid tosylate (2.08 gm) in dry dimethylformamide (DMF) (80 ml) is added N-carbobenzyloxy-glycyl-L-phenylalanine N-hydroxysuccinimide ester (1.80 gm) followed by N-methylmorpholine (803 mg). The mixture is stirred in the cold for an additional hour, then at room temperature for about 17–18 hours. The resulting solution is poured into 500 ml of 0.5 NHCl and the mixture is extracted with $2\times250$ ml of $CHCl_3$. The combined extracts are washed with a 5% $NaHCO_3$ solution, and the organic phase is dried over $MgSO_4$ and evaporated to leave a solution of DMF and product. The residual DMF is removed by co-distillation with toluene, ethylene dichloride, $CHCl_3$ and $CH_2Cl_2$ to leave 2.66 gm of a white colored foam. Trituration with ether yielded 2.56 gm of the desired product. IR and NMR analysis confirmed the product.

NMR data ($CDCl_3$) delta: 3.75(d) 2—H, 4.44(m) 1—H, 4.66 (m) 11—H, 4.92(m) 2—H, 5.40(m) 1—H, 6.55(m) 1—H, 7.00—7.30(m) 11—H, 7.35 (m) 4—H, 7.92(d) 1—H, 8.47 (d) 1—H;

IR data: ($CDCl_3$); CO, $cm^{-1}$: 1630, 1665, 1720; [alpha]$_D$ = $-19°$ ($CHCl_3$); MS $(M+1)^+ = 743$ m/z.

b) 7-(3-N-carbobenzyloxy-Gly-L-Phe-amino)-1-pyrrolidinyl]-1-(2,4-difluorophenyl)-6-fluoro-1,4-dihydro-4-oxo-1,8-naphthridine-3-carboxylic acid (2.55 gm), 10% Pd/C (dry) (1.25 gm) and 150 ml acetic acid are reacted on a Parr Shaker apparatus under 60 psi of hydrogen atmosphere for about a 24 hour period. After the reaction is completed, the hydrogen is vented, the catalyst is removed by filteration and the reaction mixture is washed thoroughly. The filtrate is evaporated to leave a residue. This residue is treated with a 0.5N HCl in ethanol solution and evaporated. The residual HCl is removed by co distillation with ethanol to leave 1.77 grams of a light yellow colored powder. NMR and IR analysis confirmed product identification. MS $(M+1)^+ = 609$ m/z. [alpha]$_D$ = $+35°$ ($CH_3OH$).

NMR data (DMSO):delta: 2.84(m) 2—H, 3.50(m) 2—H, 4.20(m) 1—H, 4.51(m) 1—H, 7.03(m) 1 H, 7.03(m) 1—H, 7.10—7.23 (m) 5—H, 7.35(m) 1—H, 7.60(m) 1—H, 7.80(m) 1—H, 8.05(m) 2—H, 8.40(m) 1—H, 11.43(s) 1—H.

IR data (KBR) CO, cm : 1630; 1670, 1710.

EXAMPLE 2

7-[3-Norvaline-amino-1-pyrrolidinyl]-1-(2,4-difluorophenyl)- 6-fluoro-1,4-dihydro-4-oxo-1,8-naphthyridine-3-carboxylic acid hydrochloride.

a) To a cold solution of 7-(3-amino-1-pyrrolidinyl)-1-(2,4-difluorophenyl)-6-fluoro-1,4-dihydro-4-oxo-1,8-naphthyridine-3-carboxylic acid tosylate (2.50 gm) in dry DMF (25 ml) is added N-carbobenzyloxy-L-Nor-Valine-N-Hydroxyphthalimide ester (1.89 gm) followed by N-methylmorpholine (1.06 gm). The mixture is stirred in the cold for an additional hour, then at room temperature for about 17-18 hours. The resulting solution is poured into 500 ml. of 0.5N HCL and the mixture is extracted with $2\times250$ ml. portion of $CHCl_3$. The combined extracts are washed with 5% $NaHC0_3$ solution and the organic phase is dried over $MgSO_4$ and evaporated to leave a solution of DMF and product. The residual DMF is removed by co distillation with toluene, with ethylene dichloride, with $CHCl_3$ and with $CH_2Cl_2$ to leave 2.69 grams of a white colored foam. Trituration with ether caused the foam to crystallize and yield 2.34g (85% of the desired product); mp=200°-202°; [alpha]$_D$=2.6° ($CHCl_3$); MS $(M+1)^+ = 638$ m/z.

NMR data ($CDCl_3$):delta: 0.90(m) 3—H, 1.35(m) 2—H, 1.61(m) 2—H, 1.80(m) 1—H, 2.00(m) 2—H, 4.20(m) 1—H, 4.50(m) 1—H, 5.05(s) 2—H, 5.40(m) 1—H, 7.05(m) 1—H, 7.30(m) 5—H, 7.85(m) 1—H, 8.40(m) 1—H.

IR data (CDCl$_3$) CO, cm$^{-1}$: 1630. 1670, 1718.

Alternately, this compound can be made by reacting 2.5 gm 7 chloro 1 (2,4-difluorophenyl)-6-fluoro-1,4-dihydro-4-oxo-1,8-naphthyridine-3-carboxylic acid with 3 gm of (3-N-carbobenzyloxy Norvalylamino)-pyrrolidine in 20 ml pyridine at 65° C. for 24 hours. The solvent was removed and the residue is treated with trifluoroacetic acid and then evaporated to remove the solvent. It is then treated with ethanol and ether and filtered yielding the 7-(3-N-carbobenzyloxy-L-Norvaline-amino-1-pyrrolidinyl-(2,4-difluorophenyl)-6-fluoro-1,4-dihydro 4-oxo-1, 8-naphthyridine-3-carboxylic acid.

(b) A mixture of 7-(3-N-carbobenzyloxy-L-Norvaline-amino-1-pyrroldinyl)-1-(2-4difluorophenyl)-6-fluoro-1,4-dihydro-4-oxo-1,8-naphthyridine-3-carboxylic acid (2.32 gm), 10% Pd/C (1.16 gm) and 150 ml acetic acid is reacted on a Parr Shaker apparatus under 60 psi of hydrogen atmosphere for about 24 hours. After the reaction is completed, the hydrogen is vented, the catalyst is removed by filtration and the reaction mixture is washed thoroughly. The filtrate is evaporated to leave a residue. This residue is treated with 0.5N HCl in ethanol and evaporated. The residual HCl is removed by co-distillation with ethanol to leave 1.94 gm of a yellow colored powder. mp=190° (dec.); [alpha]$_D$+3.7° (CH$_3$OH).

MS (M+1)$^+$=504 m/z.

NMR data (DMSO) delta: 0.85(m) 3—H, 1.25(m) 3—H, 1.63(m) 2—H, 2.05(m) 1—H, 4.32(m) 1—H, 7.35(m)1H, 7.60 (m) 1—H, 7.80(m) 1—H, 8.25(m) 2—H, 8.82(s) 1—H, 8.90(m) 1—H.

IR data (KBR) CO, cm$^{-1}$: 1630, 1680, 1772.

Alternately, the above compound can be made as follows: To a solution of 2.0 gm of ethyl 7-chloro-1-(2,4-difluorophenyl)-6-fluoro-1,4-dihydro-4-oxo-1,8-naphthyridine-3-carboxylate in 20 ml of pyrridine at 65° C. is added in 3 gm of 3-(N-t-butoxy carbonyl-Norvalylamino)-pyrrolidine. After 20 hours, the solvent is removed. The product is purified by column chromatography on silica to give ethyl 7-(3-N-t-butoxycarbonyl Norvalylamino pyrrolidin-1-yl-1-(2,4-difluorophenyl-6-fluoro-1,4-dihydro-4-oxo-1,8-naphthyridine-3-carboxylate. This compound is dissolved in 20 ml trifluoroacetic acid and 20 ml of 6N HCl is added and the mixture is refluxed for 20 hours. The solvent is removed to give 7-(3-Norvaline-amino-1-pyrrolidinyl)-1-(2,4-difluorophenyl)-6-fluoro-1,4-dihydro-4-oxo-1,8-naphthyridine-3-carboxylic acid hydrochloride.

EXAMPLE 3

7-(3-L-Norvaline-L-Norvaline amino-1-pyrolidinyl)-1-(2,4-difluorophenyl)-6-fluoro-1,4-dihydro-4-oxo-1,8-naphthyridine-3-carboxylic acid hydrochloride.

(a) To a cold solution of (3-L-Norvaline-amino-1-pyrolidinyl)-1-(2,4-difluorophenyl)-6-fluoro-1,4-dihydro-4-oxo-1,8-naphthryridine-3-carboxylic acid hydrochloride (681 mg) in dry DMF (20 ml) is added N-carbobenzyloxy-1-Norvaline-N-hydroxy-phthalimide ester (500 mg) followed by methyl-morpholine (255 mg). The mixture is stirred in the cold for an additional hour, then at room temperature for about 17-18 hours. The resulting solution is poured into 250 ml. of 0.5N HCl and the mixture is extracted with 2×200 ml portions of CHCl$_3$. The combined extracts are washed with 5% NaHCO$_3$ solution and the organic phase is dried over MgSO$_4$, and evaporated to leave a solution of DMF and product. The residual DMF is removed by co-distillation with toluene, with ethylene dichloride, CHCl$_3$ and CH$_2$Cl$_2$ to leave 768 mg of a light yellow colored foam. The residue is purified by a column chromatography (EM Sciences Silica Gel, 70-230 Mesh) to obtain 469 mg of product. [alpha]$_D$ = −2.6° (CHCl$_3$); MS (m+1)=737 m/z.

NMR data (DMSO)—delta: 0.8(m) 6—H, 1.25(m) 6—H, 1.50(m) 4—H, 3.95(m), 2—H, 4.16(m) 2—H, 4.25(m) 1—H, 4.97(m) 2—H, 7.33(m) 5—H, 7.40(m) 1—H, 7.55(m) 1—H, 7.75(m) 1—H, 7.85(m) 1—H, 8.05(m) 1—H, 8.15(m) 1—H, 8.77(m) 1—H.

IR data (CHCl$_3$) CO cm$^{-1}$: 1635, 1660, 1720.

(b) A mixture of 7-(3-N-carbobenzyloxy-L-Norvaline-L-Norvaline-amino-1-pyrrolidinyl)-1-(2,4difluorophenyl)-6-fluoro-1,4-dihydro-4-oxo-1,8-naphthyridine-3-carboxylic acid (449 mg), 10% Pd/C (dry, 225 mg) and 50 ml of acetic acid is reacted on a Parr Shaker apparatus under 60 psi of hydrogen atmosphere for about 24 hours. After the reaction is completed, the hydrogen is vented, the catalyst is removed by filtration and the reaction mixture is washed thoroughly. The filtrate is evaporated to leave a residue. This residue is treated with 0.5N HCl in ethanol and evaporated. The residual HCl was removed by co-distillation with ethanol to leave 267 mg of a light yellow colored powder. mp=218°-220° C., [alpha]D=+15.4 (CH$_3$OH), MS (M+1)$^+$=603 m/z.

NMR data (DMSO) delta: 0.82(m) 6—H, 1.25(m) 4—H, 1.63(m) 4—H, 3.77(m) 1—H, 4.24(m) 2—H, 7.33(m) 1—H, 7.57(m) 1—H, 7.80(m) 1—H, 8.10(d) 1—H, 8.20(m) 2—H, 8.40(m) 1—H, 8.61(m) 1—H, 8.82(s) 1—H.

IR data: KBR CO, cm−1 −1630, 1670, 1718.

Following the procedures of Examples 1-3 above, but substituting the appropriate solubilizing group (A) and protecting and activating groups for those used in Examples 1-3, the following compounds, together with their respective IR, NMR data and with melting points where applicable, are set forth below.

EXAMPLE 4

Using the process as described in Example 1a or 2a and substituting Phe for the solubilizing group A, yields the protected phenylalanine (Phe) compound, (I) (R$_1$=2,4 difluorophenyl, X=N, R$_3$=H, R$_2$=R$_4$=H, A=carbobenzyloxy Phe), mp=168°-170° C. [alpha]$_D$=70 (CHCl$_3$).

NMR data: (CDCl$_3$)delta: 3.05(m) 1—H, 3.10(m) 1—H, 4.40(m) 2—H, 5.03(s) 2—H, 5.45(m) 1—H, 7.05—7.35(m) 11—H, 7.90(m) 1—H, 8.40(m) 1—H IR data: (CDCl$_3$) CO, cm$^{-1}$: 1 1630, 1670, 1718.

EXAMPLE 5

Using the process as described in Example 2b with the compound of Example 4 yields the deblocked Phe (HCl) salt, (I)(R$_1$=2,4 difluorophenyl, X=N, R$_2$=R$_3$=R$_4$=H, A=Phe), mp=188°-190° C. M.S. (M+1)=552 m/z. [alpha]$_D$=9.2 (CH$_3$OH).

NMR data: (DMSO)delta: 2.90(m) 1—H. 3.06(m) 1—H. 3.90(m) 1—H. 4.24(m) 1—H. 7.10(m) 2—H. 7.20—7.40(m) 5—H. 7.60(m) 1—H. 7.82(m) 1—H. 8.10(m) 1—H, 8.40(m) 2—H, 8.83(m) 1—H IR data: (KBR) CO, cm−: 1630, 1682, 1720.

EXAMPLE 6

Using the process as described in Example 2a and substituting Gly for the solubilizing group A, yields the protected Gly compound, (I)($R_1$=2,4-difluorophenyl, X=N, $R_2$=$R_3$=$R_4$=H, A=carbobenzyloxygly), mp=179°-182° C. MS (M+1)$^+$=596m/z.

NMR data: (CDCl3)delta: 2.05(m) 1—H, 3.92(m) 2—H, 4.59(m) 1—H, 5.06(s) 2—H, 5.50(m) 1—H, 7.04(m) 2—H, 7.28(m) 5—H, 7.75(m) 1—H, 8.32(m) 1—H.

IR data: (CDCl3) CO, cm$^{-1}$: 1630, 1678, 1720.

EXAMPLE 7

Using the process as described in Example 2b with the compound of Example 6 yields the deblocked Gly (HCl) salt, (I)($R_1$=2,4 difluorophenyl, X=N, $R_2$=$R_3$=$R_4$=H, A=Gly), mp=195°-198° C. MS (M+1)$^+$=462 m/z.

NMR data: (DMSO) delta: 3.50(d) 2—H, 4.32(m) 1—H, 7.35(m) 1—H, 7.60(m) 1—H, 7.82(m) 1—H, 8.10(m) 2—H, 8.77(d) 1—H, 8.83(s) 1—H.

IR data: (KBR) CO, cm$^{-1}$: 1633, 1670, 1733.

EXAMPLE 8

Using the process as described in either Example 1a or 3a and substituting Phe-Gly for the solubilizing group A, yields the protected Phe-Gly compound (I)($R_1$=2,4 difluorophenyl, X=N, $R_2$=$R_4$=$R_3$=H, A=carbobenzyloxy Phe Gly). MS (M+1)$^+$=828 m/z. [alpha]$_D$=4.7 (CHCl3)

NMR data: (CDCl3) delta: 2.05(m) 2—H, 2.97(m) 1—H, 3.13(m) 1—H, 3.40(d) 1—H, 4.23(m) 1—H, 4.50(m) 1—H, 4.89(m) 2—H, 5.22(m) 1—H, 7.05—7.35(m) 16—H, 7.88(d) 1—H, 8.45(m) 1—H.

IR data: (CDCl3) CO, cm$^{-1}$: 1635, 1670, 1710.

EXAMPLE 9

Using the process as described in Example 3b with the compound of Example 8 yields the deblocked Phe-Gly(HCl) salt (I)($R_1$=2,4-difluorophenyl, X=N, $R_2$=$R_3$=$R_4$=H, A=Phe-Gly).

NMR data: (DMSO) delta: 1.85(m) 1-H, 2.05(m) 1—H, 2.95(m) 1—H, 3.10(m) 1—H, 3.75(m) 2—H, 4.05(m) 1—H, 4.30(m) 1—H, 7.27(m) 4—H, 7.60(m) 1—H, 7.70(m) 1—H, 8.10(m) 1—H, 8.35(m) 1—H, 8.82(s) 1—H.

IR data: KBr CO, cm$^{-1}$: 1630, 1680, 1720.

EXAMPLE 10

Using the process as described in either Example 1a or 3a and substituting Ala Phe for the solubilizing group A, yields the protected Ala-Phe compound (I)($R_1$=2,4 difluorophenyl, $R_2$=$R_3$=$R_4$=H, X=N, A=carbobenzyloxy Ala-Phe). MS (M+1)$^+$=757 m/z.

NMR data: (CDCl3,>delta: 1.25(m) 3—H, 2.05(m) 1—H, 3.13(m) 3-H, 4.00(m) 1—H, 4.46(m) 1—H, 4.62(m) 1—H, 4.86(m) 1—H, 4.86(m) 1—H, 5.05(m) 1—H, 6.41(m) 1—H, 7.00 7.40(m) 14—H, 7.96(m) 1—H, 8.52(m) 1—H.

EXAMPLE 11

Using the process as described in Example 3b with the compound of Example 10 yields the deblocked Ala-Phe (HCl) salt, (I)($R_1$=2,4-difluorophenyl, X=N, $R_2$=$R_3$=$R_4$=H, A=Ala-Phe), mp 195°-198° C.; [alpha]=+45.2 (CH3OH). MS (M+1)$^+$=623 m/z.

IR (KBr) CO, cm$^{-1}$: 1630, 1670, 1720.

NMR data: (CD3OD) delta: 1.47(m) 3—H, 1.90(m) 1—H, 2.96(m) 2—H, 3.90(m) 1—H, 4.23(m) 1—H, 4.53(m) 1—H, 6.98(m) .1—H, 7.07(m) 1—H, 7.15(m) 1—H, 7.25(m) 5—H, 7.65(m) 1—H, 8.05(m) 1—H, 8.78(m) 1—H.

EXAMPLE 12

Using the process as described in Example 1a or 2a and substituting Tyr for the solubilizing group A yields the protected Tyr compound, (I)($R_1$=2,4-difluorophenyl, X=N, $R_2$=$R_3$=$R_4$=H, A=carbobenzyloxy Tyr). MS (M+1)$^+$=702 m/z.

NMR data: (DMSO) delta: 1.62(m) 1—H, 1.96(m) 1—H, 2.64(m) 1—H, 4.08(m) 1—H, 4.23(m) 1—H, 6.53(m) 1—H, 6.62(m) 1—H, 6.42—7.02(m) 2—H, 7.25 7.38(m) 5—H, 7.45(m) 1—H, 7.60(m) 1—H, 7.80(m) 1—H, 8.10(m) 2—H.

IR data: (CHCl3) CO, cm$^{-1}$: 1630, 1670, 1718.

EXAMPLE 13

Using the process as described in Example 1b or 2b with the compound of Example 12 yields the deblocked Tyr (HCl) salt, (I)($R_1$=2,4 difluorophenyl, X=N, $R_2$=$R_3$=$R_4$=H, A=Tyr), MS (M+1)$^+$=568 m/z.

NMR data: (DMSO)delta: 1.56(m) 1—H, 1.97(m) 1—H, 2.87(m) 1—H, 3.80(m) 1—H, 4.24(m) 1—H, 6.50(m) 1—H, 6.69(m) 1—H, 6.86(m) 2—H, 6.97(m) 1—H, 7.17(m) 1—H, 7.33(m) 1—H, 7.60(m) 1—H, 7.80(m) 1—H, 8.08(d) 1—H, 8.27(m) 2—H, 8.62(m) 1—H, 8.82(m) 1—H, 9.22(m) 1—H, 9.40(m) 1—H, 9.80(m) 1—H IR data: (KBr) CO, cm$^{-1}$ 1 1635, 1683, 1720.

EXAMPLE 14

Using the process as described in either Example 1 or 3a and substituting Ala Ala for the solubilizing group A yields the protected Ala-Ala compound (I)($R_1$=2,4 difluorophenyl, X=N, $R_2$=$R_3$=$R_4$=H, A=carbobenzyloxy Ala-Ala). MS (M+1)$^+$=681 m/z. [alpha]$_D$=−12.1° C. (CHCl3) or 4.0 (DMSO), mp 160°-164° C.

NMR data: delta: 1.37(m) 6—H, 2.00(m) 2—H, 3.40(m) 2—H, 4.07(m) 1—H, 4.45(m) 2—H, 4.96(m) 2—H, 5.20(m) 1—H, 6.46(m) 1—H, 7.06(m) 2—H, 7.33(m) 5—H, 7.43(m) 1—H, 8.50(d) 1—H.

IR data: (CDCl3) CO cm$^{-1}$: 1 1630, 1670, 1719.

EXAMPLE 15

Using the process as described in Example 3b with the compound of Example 14 yields the deblocked Ala-Ala (HCl) salt, (I)($R_1$=2,4-difluorophenyl, X=N, $R_2$=$R_3$=$R_4$=H, A=Ala-Ala), mp =202°-205° C., [alpha]$_D$=10.4° (CH3OH); MS (M+1)$^+$=547 m/z.

NMR data (DMSO)delta: 1.20(t) 3—H, 1.30(d) 3—H, 1.80 (m) 2—H, 2.03(m) 2—H, 3.83(m) 2—H, 4.24(m) 2—H, 7.33(m) 1—H, 7.58(m) 1—H, 7.80(m) 1—H, 8.15(m) 2—H, 8.36(m) 1—H, 8.61(m) 1—H, 8.82(s) 1—H.

EXAMPLE 16

Using the process as described in Example 1a or 2a and substituting Ala for the solubilizing group A yields the protected alanine (Ala) compound, (I) ($R_1$=2.4 difluorophenyl, X=N, $R_3$=H, $R_2$=$R_4$=H, A=carbobenzyloxy Ala); mp=173°-174° C., [alpha]$_D$=1.80 (CHCl3). MS (M+1)=610 m/z NMR data: (CDCl3)delta: 1.38(m), 3—H, 2.00(m) 2—H, 4.25(m) 1—H, 4.54(m) 1—H; 5.06(s) 2—H, 5

42(m) 1—H, 7.04(m) 1—H, 7.13(m) 1—H, 7.30(m) 5—H,
7.90(m) 1—H.
IR data: (CDCl$_3$) CO, cm$^{-1}$: 1630, 1670, 1720.

EXAMPLE 17

Using the process as described in Example 2b with the compound of Example 16 yields the deblocked Ala (HCl) salt, (I)(R$_1$=2,4 difluorophenyl, X=N, R$_2$=R$_3$=R$_4$=H, A=Ala), mp=202°-205° C. M.S. (M+1) 476 m/z. [alpha]$_D$=5.6 (CH$_3$OH).

NMR data: (DMSO)delta: 1.32(t) 3—H, 1.85(m) 1—H, 2.05(m) 1—H, 3.75(m) 1—H, 4.32(m) 1—H, 7.35(m) 1—H, 7.60(m) 1—H, 7.80(m) 1—H, 8.09(D) 1—H, 8.20(m) 2—H, 8.80(m) 1—H, 8.83(m) 1—H IR data: (KBR) CO, cm$^{-1}$: 1635, 1680, 1720.

EXAMPLE 18

Using the process as described in Example 2a and substituting Val for the solubilizing Group A yields the protected Val compound, (I)(R$_1$=2,4-difluorophenyl, X=N, R$_2$=R$_3$=R$_4$=H, A=carbobenzyloxyVal), mp=170° C. (dec), MS (M+1)$^+$=638m/z [alpha]$_D$=2.1° (CHCl$_3$).

NMR data (CDCl$_3$)delta: 0.90(m) 3—H, 0.95(m) 2—H, 2.00(m) 2—H, 2.20(m) 2H, 3.40(m) 2H, 4.10(m) 2—H, 4.55(m) 1—H, 5.05(m) 2H, 45(m) 1—H, 7.00(m) 1—H, 7.30(s) 5—H, 8.40(m) 1—H, 8.40(m) 1—H.

IR data: (CDCl$_3$) CO, cm$^{-1}$: 1630, 1670, 1720.

EXAMPLE 19

Using the process as described in Example 2b with the compound of Example 18 yields the deblocked Val (HCl) salt, (I)(R$_1$=2,4 difluorophenyl, X=N, R$_2$=R$_3$=R$_4$=H, A=Val); mp=195°-198° C., MS (M+1)=504 m/z. [alpha]$_D$=11.2° (CH$_3$OH).

NMR data: DMSO(delta): 0.85(m) 3H, 1.85(m) 1—H, 2.05(m) 2—H, 4.35(m) 1H, 7.35(m) 1—H, 7.70(m) 1H, 7.80(m) 1H, 8.10(D) 1H, 8.80(m) 1H, 8.82(S) 1H.

IR data: (KBR) CO, cm$^{-1}$− 1630, 1680, 1720.

EXAMPLE 20

Using the process as described in Example 2a and substituting Leu for the solubilizing group A yields the protected Leucine compound (I)(R$_1$=2,4-difluorophenyl, X=N, R$_2$=R$_4$=R$_3$=H, A=carbobenzyloxy Leu). MS (M+1)$^+$=652 m/z, m.p.=188°-190° C., [alpha]$_D$=−7.9° (CHCl$_3$)

NMR data: (CDCl$_3$) delta: 0.90(S) 3H, 1.50(m) 1H, 1.65(S) 2H, 2.00(m) 2H, 3.45(m) 2H, 3.85(m) 1—H, 4.20(m) 1H, 4.50(m) 1H, 5.05(S) 2H, 5.30(m) 1H, 7.05(m) 1H, 7.15(m) 1H, 7.30(S) 5H, 7.85(m) 1H, 8.40(m) 1H.

IR data: (CDCl$_3$) CO, cm$^{-1}$ 1630, 1670, 1720.

EXAMPLE 21

Using the process as described in Example 2b with the compound of Example 20 yields the deblocked Leu(HCl) salt (I)(R$_1$=2,4-difluorophenyl, X=N, R$_2$=R$_3$=R$_4$=H, A =Leu). mp=198° C. (decomposition), MS (M+1)$^+$518 m/z [alpha]$_D$=3.0° (CH$_3$OH).

NMR data: (DMSO) delta: 0.85(m) 3H, 1.50(m) 2H, 1.85(m) 1H, 2.05(m) 1H, 3.65(m) 1H, 4.30(m) 1H, 7.35(m) 1H, 7.60(m) 1H, 7.80(m) 1H, 8.10(D) 1H, 8.25(m) 2H, 8.82(S) 1H, 8.90(m) 1H.

IR data: KBr CO, cm$^{-1}$ 1630, 1680, 1730.

EXAMPLE 22

Using the process as described in Example 2a and substituting Met for the solubilizing group A yields the protected Methionine compound (I)(R$_1$=2,4-difluorophenyl, R$_2$=R$_3$=R$_4$=H, X=N, A=carbobenzyloxy Met).

EXAMPLE 23

Using the process as described in Example 2b with the compound of Example 22 yields the deblocked Met (HCl) salt, (I)(R$_1$=2,4-difluorophenyl, X=N, R$_2$=R$_3$=R$_4$=H, A=Met), MS (M+1)$^+$=536; [alpha]$_D$4.1° (CH$_3$OH).

NMR data DMSO data: 1.95(S) 3H, 2.05(D) 2H, 2.45(m) 2H, 3.75(m) 1H, 4.30(m) 1—H, 7.35(m) 1H, 7.60(m) 1H, 7.80(m) 1H, 8.10(D) 1H, 8.25(m) 2H, 8.32(S) 1H, 8.35(m) 1H.

IR data: KBR CO, cm$^{-1}$ 1630, 1680, 1730.

EXAMPLE 24

1-(2,4-Difluorophenyl)-6-Fluoro-7-(3-Gly-L-Phe -Amino 1-Pyrrolidinyl)-1,4-Dihydro-4-Oxo-Quinoline-3-Carboxylic Acid Hydrochloride (a) To a cold suspension of 701 mg 1-(2,4-difluorophenyl)-6-fluoro-7-(3-amino-1-pyrrolidinyl)-1,4-dihydro-4-oxoguinoline-3-carboxylic acid hydrochloride in 30 ml of dry DMF is added 795 mg of N-carbobenzyloxyglycyl-phenylalanine N-hydroxysuccinimide ester followed by 354 mg of N-methylmorpholine. The mixture is stirred in the cold for an additional hour, then at room temperature overnight. The resulting solution is poured into 200 ml of 0.5 NHCl and the mixture is extracted with 2×150 ml portions of CHCl$_3$. The combined extract is washed with 5% NaHCO$_3$ solution and the organic phase is dried over MgSO$_4$, evaporated to leave a solution of DMF and product. The residual DMF is removed by co-distillation with toluene with ethylene dichloride, with CHCl$_3$ and with CH$_2$Cl$_2$ to leave 1.21 grams of a yellow colored foam. Trituration with IPA caused the foam to crystallize. Yield 936 mg (79%), mp=125°-128° C., [delta]$_D$=−16.5° (CHCl$_3$)

NMR data, CDCl$_3$ delta: 1 65(s) 2H, 2.00(m) 2H, 3.10(m) 2H, 3.50(m) 1H, 3.75(m) 2H, 4.50(m) 1H, 4.75(m) 1H, 4.98(s) 2H, 5.40(m) 1H, 5.65(m) 1H, 6.60(m) 1H, 7.10(m) 1H, 7.25(m) 10H, 7.50(m) 1H, 7.70(m) 1H, 8.11(s) 1H, 8.20(m) 1H, 8.25(D) 1H.

IR data: (CDCl$_3$) CO, cm$^{-1}$ 1630, 1680, 1720.

(b) 891 mg of 1-(2,4 -difluorophenyl)-6-fluoro-7-(3-N-carbobenzyloxygly-phe-amino-1-pyrrolidinyl)-1,4-dihydro-4-oxoguinoline-3-carboxylic acid from Example 24(a) above, 0.45 grams of 10% Pd/C (Dry) and 50 ml of Acetic Acid is reacted on a Parr Shaker Apparatus under 60 psi of hydrogen atmosphere for 24 hours. After the reaction is completed, the hydrogen is vented, the catalyst is removed by filtration and washed thoroughly. The filtrate is evaporated to leave a residue. This residue is treated with 0.5NHCl in ethanol and evaporated. The residual HCl is removed by co-distillation with ethanol to leave a yellow colored solid yield 708 mg (91%) the title compound. mp=205° C. (dec), [delta]$_D$ +35.9 (CH$_3$OH)

NMR data, DMSO delta: 1.23(S) 2H, 1.60(m) 2H, 1.75(m) 1H, 2.00(m) 2H, 2.85(m) 2H, 4.20(m) 2H, 4.50(m) 1H, 5.75(m) 1H, 7.20(m) 6H, 7.50(m) 1H, 7.80(m) 1H, 8.05(m) 2H, 8.40(m) 1H, 8.75(m) 1H, 8.77(S) 1H.

IR Data (KBR) CO cm$^{-1}$ 1635, 1670, 1720

EXAMPLE 25

Using the process as described in Example 24a, using or replacing 1-(2,4-difluorophenyl)-6-fluoro-7-(3-amino-1-pyrrolidinyl)-1,4-dihydro-4-oxoquinoline-3-carboxylic acid with an appropriate quinolone and naphthyridine derivative such as 1-(4-fluorophenyl)-6-fluoro-7-(3-amino-1-pyrrolidinyl)-1,4-dihydro-4-oxoquinoline-3-carboxylic acid, 1-(4-fluorophenyl)-6-fluoro-7-(3-amino-1-pyrrolidi nyl-1,4-dihydro-4-oxo-1,8-naphthyridine-3-carboxylic acid, 1-cyclopropyl-6-fluoro-7-(3-amino-1-pyrrolidinyl)-1,4-dihydro-4-oxo quinoline-3-carboxylic acid, 1-cyclopropyl-6-fluoro-7-(3-amino-1-pyrrolidinyl)-1,4-dihydro-4-oxo-1,8-naphthyridine-3-carboxylic acid, 1-cyclopropyl-6,8-difluoro-7-(3-amino-1-pyrrolidinyl)-1,4-dihydro-4-oxo-quinoline-3-carboxylic acid, 1-cyclopropyl 7-(3-amino-1-pyrrolidinyl)-6-fluoro-8-chloro-1,4-dihydro-4-oxo-quinoline-3-carboxylic acid, 1-cyclopropyl-7-(3-amino 1-pyrrolidinyl)-5-amino-6,8-difluoro-1,4-dihydro-4-oxoquinoline-3-carboxylic acid, 1-t-butyl-7-(3-amino-1-pyrrolidinyl)-6-fluoro-1,4-dihydro-4-oxoquinoline-3-carboxylic acid, 1t-butyl-7-(3-amino-1-pyrrolidinyl)-6,8-difluoro 1,4-dihydro-4-oxoquinoline-3-carboxylic acid, 1-t-butyl-7-(3-amino-1-pyrrolidinyl)-6-fluoro-1,4-dihydro-4-oxo-1,8-naphthyridine-3-carboxylic acid, 1-(2-fluoroethyl)-7-(3-amino-1-pyrrolidinyl)-6-fluoro-1,4-dihydro-4-oxoquinoline-3-carboxylic acid, 1-(2-fluoroethyl)-7-(3-amino-1-pyrrolidinyl)-6,8-difluoro-1,4-dihydro-4-oxoquinoline-3-carboxylic acid, 1-(2-fluoroethyl)-7-(3-amino-1-pyrrolidinyl)-6-fluoro-1,4-dihydro-4-oxo-1,8-naphthyridine-3-carboxylic acid, 1-ethyl-7-(3-amino 1-pyrrolidinyl) 6-fluoro-1,4-dihydro-4-oxoquinoline-3-carboxylic acid or 1-ethyl-7-(3-amino-1-pyrrolidinyl)-6-fluoro-1,4-dihydro-4-oxo-1,8-naphthyridine-3-carboxylic acid, 1-cyclopropyl-6-fluoro-7-(3-amino-1-pyrrolidinyl)-8-methyl-1,4-dihydro-4-oxo-quinoline-3-carboxylic acid and substituting various amino acids or peptides for one solubilizing group A, the following compounds as shown in the Table I are made.

TABLE I

| | Starting Material | | | Reactant | | Resultant Compound | | |
|---|---|---|---|---|---|---|---|---|
| | X | $R_1$ | $R_3$ | A | A | X | $R_1$ | $R_3$ |
| a | CH | 2,4-difluorophenyl | H | Phe | Phe | CH | 2,4-difluorophenyl | H |
| b | CH | " | H | Nval | Nval | CH | " | H |
| c | CH | " | H | Ala | Ala | CH | " | H |
| d | CH | " | H | NvalNval | NvalNval | CH | " | H |
| e | CH | " | H | Gly | Gly | CH | " | H |
| f | CH | " | H | Val | Val | CH | " | H |
| g | CH | " | H | Leu | Leu | CH | " | H |
| h | CH | 4-fluorophenyl | H | Nval | Nval | CH | 4-fluorophenyl | H |
| i | N | " | H | Nval | Nval | N | " | H |
| j | CH | cyclopropyl | H | Met | Met | CH | cyclopropyl | H |
| k | CH | " | H | Gly—Phe | Gly—Phe | CH | " | H |
| l | CH | " | H | Nval | Nval | CH | " | H |
| m | CH | " | H | Leu | Leu | CH | " | H |
| n | CH | " | H | Val | Val | CH | " | H |
| o | N | " | H | Leu | Leu | N | " | H |
| p | N | " | H | Nval | Nval | N | " | H |
| q | N | " | H | Val | Val | N | " | H |
| r | CF | cyclopropyl | H | Nval | Nval | CF | cyclopropyl | H |
| s | CF | " | H | Ala | Ala | CF | " | H |
| t | CCL | " | H | Ala | Ala | CCL | " | H |
| u | CCL | " | H | Leu | Leu | CCL | " | H |
| v | CCL | " | H | Nval | Nval | CCL | " | H |
| w | CCL | " | H | Phe | Phe | CCL | " | H |
| x | CF | " | $NH_2$ | Nval | Nval | CF | " | $NH_2$ |
| y | CF | " | $NH_2$ | Ala | Ala | CF | " | $NH_2$ |
| z | CH | t-butyl | H | Nval | Nval | CH | t-butyl | H |
| aa | CH | " | H | Ala | Ala | CH | " | H |
| bb | N | " | H | Nval | Nval | N | " | H |
| cc | N | " | H | Ala | Ala | N | " | H |
| dd | CF | " | H | Nval | Nval | CF | " | H |
| ee | CH | ethyl | H | Nval | NVal | CH | ethyl | H |
| ff | N | " | H | Nval | Nval | N | " | H |
| gg | CH | 2-fluoroethyl | H | Nval | Nval | CH | 2-fluoroethyl | H |
| hh | CF | " | H | Nval | Nval | CF | " | H |
| ii | $CCH_3$ | cyclopropyl | H | Nval | Nval | $CCH_3$ | cyclopropyl | H |
| jj | CH | 2,4-difluorophenyl | H | GlyPhe | GlyPhe | CH | 2,4-difluorophenyl | H |
| kk | N | cyclopropyl | H | NvalNval | NvalNval | N | cyclopropyl | H |
| ll | N | " | H | GlyGly | GlyGly | N | " | H |
| mm | N | " | H | GlyNval | GlyNval | N | " | H |
| nn | CH | " | H | NvalNval | NvalNval | CH | " | H |
| oo | CH | " | H | GlyGly | GlyGly | CH | " | H |

Z = carbobenzyloxy

TABLE I-continued

| | | | | | | | | |
|---|---|---|---|---|---|---|---|---|
| pp | CH | " | H | GlyNval | GlyNval | CH | " | H |
| qq | N | " | H | GlyGlyGly | GlyGlyGly | N | " | H |
| rr | CH | " | H | GlyGlyGly | GlyGlyGly | CH | " | H |

Table IA

The physical data for the products in the designated Examples is as follows:

EXAMPLE 25b mp.=195°-197° C.,
MS $(m+1)^+ = 637$ m/z.
$[alpha]_D = +19.5$ (CHCl$_3$)
IR (CDCl$_3$) CO, cm$^{-1}$: 1630, 1670, 1720.
NMR(CDCl$_3$) delta: 0.90 (m) 3H, 1.35 (m) 2H, 1.82 (m) 1H, 2.10 (m) 2H, 2.20 (m) 1H, 3.07 (m) 1H, 3.24 (m) 1H, 3.75 (m) 1H, 3.90 (m) 2H, 4.25 (m) 2H, 4.56 (m) 2H, 5.05 (s) 2H, 5.47 (m) 1H, 5.72 (m) 1H, 7.25 (m) 7H, 7.73 (m) 1H, 8.03 (m) 1H, 8.32 (m) 1H.

EXAMPLE 25 h mp.=182°-184° C.,
MS $(m+1)^+ = 619$ m/z.
$alpha]_D = +22.8$ (CHCl$_3$).
IR (CDCl$_3$) CO, cm$^{-1}$: 1630, 1670, 1720
NMR (CDCl$_3$) delta. 0.90 (m) 3H, 1.35 (m) 2H, 1.63 (m) 2H, 1.81 (m) 1H, 2.05 (m) 2H, 2.18 (m) 1H, 3.20 (m) 1H, 3.35 (m) 1H, 3.75 (m) 2H, 4.30 (m) 1H, 4.50 (m) 1H, 4.60 (m) 1H, 5.05 (s) 2H, 5.47 (d) 1H, 5.55 (d) 1H, 5.78 (m) 1H, 7.25 (m) 7H, 7.45 (m) 1H, 7.70 (d) 1H, 7.90 (m) 1H, 8.00 (m) 1H, 8.10 (2 s) 1H.

EXAMPLE 25i mp=186°-188° C.,
MS $(m+1)^+ = 620$ m/z.
$[alpha]_D = +10.6$ (CHCl$_3$).
IR (CDCl$_3$) CO, cm$^{-1}$: 1630, 1680, 1725.
NMR (CDCl$_3$) delta: 0.82 (m) 3H, 1.25 (m) 2H, 1.45 (m) 2H, 1 75(m) 1H, 2 00(m) 1H, 3.87 (m) 2H, 4.23(m) 1H, 4.98 (s) 2H, 7.33 (m) 7H, 7.65 (m) 2H, 8.07 (d) 1H, 8.20 (m) 1H, 8.65 (s) 1H.

EXAMPLE 25l mp. =195°-197° C.,
MS $(m+1)^+ = 565$ m/z.
$[alpha]_D = +16.7$ (CHCl$_3$).
IR (CDCl$_3$) CO, cm$^{-1}$: 1630, 1665, 1720.
NMR (CDCl$_3$) delta: 0.90 (m) 3H, 1.30 (m) 4H, 1.87 (m) 1H, 2.15 (m) 1H, 2.33 (m) 1H, 3.46 (m) 1H, 3.60 (m) 2H, 3.92 (m) 1H, 4.35 (m) 1H, 5.05 (s) 2H, 6.72 (m) 1H, 7.25 (m) 5H, 7.63 (d) 1H, 7.98 (d) 1H, 8.25 (m) 1H.

EXAMPLE 25o mp=102°-104° C.
MS $(m+1)^+ = 580$ m/z.
$[alpha]_D = +1.3$ (CHCl$_3$).
IR (CDCl$_3$) CO, cm$^{-1}$: 1630, 1670, 1710.
NMR(CDCl$_3$) delta: 0.90 (m) 6H, 1.20(m) 2H, 1.58 (m) 2H, 2.15 (m) 2H, 3.60 (m) 1H, 4.07 (m) 2H, 4.35 (m) 1H, 4.70 (m) 1H, 5.05 (s) 2H, 5.42 (m) 1H, 7.25 (m) 5H, 7.75 (d) 1H, 8.05 (m) 1H, 15.80 (s) 1H.

EXAMPLE 25p mp.=103°-105° C.
MS $(m+1)^+ = 566$ m/z.
$[alpha]_D = +7.8$ (CHCl$_3$)
IR (CDCl$_3$) CO, cm$^{-1}$1630, 1670, 1720.
NMR(CDCl$_3$) delta: 0.90 (m) 3H, 1.20(m) 2H, 1.40 (m) 2H, 1.70 (m) 2H, 1.90 (m) 1H, 2.20 (m) 2H, 3.60 (m) 1H, 4.10 (m) 2H, 4.30 (m) 1H, 4.70 (m) 2H, 5.05 (s) 2H, 5.50 (d) 1H, 7.25 (m) 6H, 7.75 (d) 1H, 8.05 (s) 1H.

EXAMPLE 25r mp.=188°-190° C.
MS $(m+1)^+ = 583$ m/z.
$[alpha]_D = +11.8$ (CHCl$_3$).
IR (KBr) CO, cm$^{-1}$: 1630, 1680, 1730.
NMR(DMSO) delta: 0.84 (m) 3H, 1.16 (m) 3H, 1.30 (m) 2H, 1.52 (m) 2H, 1.86 (m) 1H, 2.10 (m) 1H, 3.50 (m) 1H, 3.75 (m) 1H, 3.96 (m) 2H, 4.08 (m) 1H, 4.30 (m) 1H, 5.00 (2-s) 2H, 7.35 (m) 5H, 7 72 (m) 1H, 8.25 (m) 1H, 8.61 (s) 1H

EXAMPLE 25s mp.=206°-208° C.
MS $(m+1)^+ = 555$ m/z.
$[alpha]_D = +19.5$ (CHCl$_3$).
IR (CDCl$_3$) CO, cm$^{-1}$: 1620, 1665, 1720.
NMR(CDCl$_3$) delta: 1.20 (m) 5H, 1.45 (m) 3H, 2.08 (m) 2H, 2.22 (m) 1H, 3.85 (m) 6H, 4 35 (m) 1H, 4.54 (m) 1H, 5.10 (2s) 2H, 5.65 (m) 1H, 7.25 (m) 5H, 7.60 (d) 1H, 7.75 (m) 1H, 8.20 (2s) 1H.

EXAMPLE 25ff mp.=112°-114° C.
MS $(m+1)^+ = 554$ m/z.
$[alpha]_D = +8.5$ (CHCl$_3$).
IR (KBr) CO, cm$^{-1}$: 1630, 1675, 1720
NMR(DMSO) delta: 0.80 (m) 3H, 1.25 (m) 2H, 1.36 (m) 2H, 1.50 (m) 2H, 1.90 (m) 1H, 2.15 (m) 1H, 3.70 (m) 1H, 3.92 (m) 4H, 4.45 (m) 4H, 5.00 (2 s) 2H, 7.35 (m) 5H, 8.00 (d) 1H, 8.30 (m) 1H, 8.93 (s) 1H.

EXAMPLE 25jj mp=125°-128° C.
MS $(m+1)^+ = 742$ m/z.
$[alpha]_D = -16.5$ (CHCl$_3$).
IR (CDCl$_3$) CO, cm$^{-1}$: 1630, 1665, 1680, 1717.
NMR (CDCl$_3$) delta: 1.65 (s) 3H, 1.95 (m) 2H, 3.12 (m) 3H, 3.50 (m) 1H, 3.75 (m) 3H, 4.46 (m) 1H, 4.75 (m) 1H, 5.02 (2-s) 2H, 5.40 (m) 1H, 5.77 (m) 1H, 6.57 (m) 1H, 7.23 (m) 12H, 7.72 (m) 2H, 8/13 (s) 1H, 8.24 (m) 1H.

EXAMPLE 26

Using the process as described in Example 24(b), the compounds of Example 25 (a-jj) yield the following corresponding quinolone and naphthyridine derivatives (a-jj) and their hydrochloride salts as shown in Table II.

TABLE II

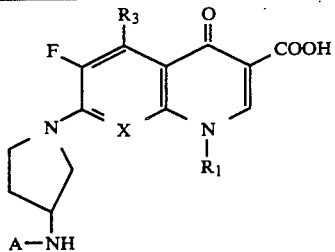

| | A | X | R₁ | R₃ |
|---|---|---|---|---|
| a | Phe | CH | 2,4-difluorophenyl | H |
| b | Nval | CH | " | H |
| c | Ala | CH | " | H |
| d | Nval—Nval | CH | " | H |
| e | Gly | CH | " | H |
| f | Val | CH | " | H |
| g | Leu | CH | " | H |
| h | Nval | CH | 4-fluorophenyl | H |
| i | Nval | N | " | H |
| j | Met | CH | cyclopropyl | H |
| k | Gly—Phe | CH | " | H |
| l | NvaL | CH | " | H |
| m | Leu | CH | " | H |
| n | Val | CH | cyclopropyl | H |
| o | Leu | N | " | H |
| p | Nval | N | " | H |
| q | Val | N | " | H |
| r | Nval | CF | " | H |
| s | Ala | CF | " | H |
| t | Ala | CCL | " | H |
| u | Leu | CCL | " | H |
| v | Nval | CCL | " | H |
| w | Phe | CCL | " | H |
| x | Nval | CF | " | NH₂ |
| y | Ala | CF | " | NH₂ |
| z | Nval | CH | t-butyl | H |
| aa | Ala | CH | " | H |
| bb | Nval | N | " | H |
| cc | Ala | N | " | H |
| dd | Nval | CF | " | H |
| ee | Nval | CH | ethyl | H |
| ff | Nval | N | " | H |
| gg | Nval | CH | 2-fluoroethyl | H |
| hh | Nval | CF | " | H |
| ii | Nval | CCH₃ | cyclopropyl | H |
| jj | GlyPhe | CH | 2,4-difluorophenyl | H |
| kk | NvalNval | N | cyclopropyl | H |
| ll | GlyGly | N | " | H |
| mm | GlyNval | N | " | H |
| nn | NvalNval | CH | " | H |
| oo | GlyGly | CH | " | H |
| pp | GlyNval | CH | " | H |
| qq | GlyGlyGly | N | " | H |
| rr | GlyGlyGly | CH | " | H |

Table IIA

The physical data for the hydrochloride salt of the products in the designated Examples is as follows:

EXAMPLE 26b mp.=205° C. (dec.),
MS (m+1)⁺ 503 m/z.
[alpha]$_D$= +8.3 (CH₃OH).
IR (KBr) CO, cm⁻¹: 1630, 1683, 1730.
NMR(DMSO) delta: 0.85 (m) 3H, 1.26 (m) 3H, 1.63 (m) 2H, 1.90 (m) 1H, 2.10 (m) 1H, 3.67 (m) 2H, 4.34 (m) 1H, 5.82 (d) 1H, 7.45 (m) 1H, 7.75 (m) 1H, 7.92 (m) 2H, 8.21 (m) 2H, 8 75 (s) 1H, 8.85 (m) 1H.

EXAMPLE 26h mp.=196°-198° C.
MS (m+1)⁺ =485 m/z.
[alpha]$_D$= +11.9 (MeOH).
IR (KBr) CO cm⁻¹: 1630, 1680, 1720.
NMR (DMSO) delta: 0.85 (m) 3H, 1.23 (m) 2H, 1.65 (m) 2H, 1.90 (m) 2H, 2.10 (m) 2H, 3 65 (m) 2H, 4.33 (m) 1H, 5.88 (d) 1H, 7.55 (m) 2H, 7.75 (m) 2H, 7.90 (d) 1H, 8.20 (m) 2H, 8.55 (s) 1H, 8.86 (d) 1H.

EXAMPLE 26i mp.=208°-210° C.
MS (m+1)⁺=486 m/z.
[alpha]$_D$= +6.0 (meOH).
IR(KBr) CO, cm⁻¹: 1630, 1680, 1730 .
NMR (DMSO) delta: 0.85 (m) 3H, 1.25 (m) 3H, 1.64(m) 2H, 1.85(m) 1H, 2.08(m) 1H, 3.65 (m) 1H, 4.32 (m) 1H, 7.43 (m) 2H, 7.67 (m) 2H, 8.08 (d) 1H, 8.22 (m) 2H, 8.65 (s) 1H, 8.85 (m) 1H.

EXAMPLE 26l mp.=202°-204° C.
MS (m+1)⁺ =431 m/z.
[alpha]$_D$= +23.1 (DMSO).
IR (KBr) CO, cm⁻¹: 1630, 1680, 1720.
NMR (DMSO) delta: 0.85 (m) 3H, 1.15 (m) 3H, 1.30 (m) 4H, 1.70 (m) 2H, 2.00 (m) 2H, 2.25 (m) 1H, 3.55 (m) 1H, 3.75 (m) 4H, 3.90 (m) 1H, 4.45 (m) 1H, 7.06 (m) 1H, 7.81 (d) 1H, 8.30 (m) 2H, 8.58 (s) 1H, 9.03 (m) 1H.

EXAMPLE 26o mp=204°-206° C.
MS (m+1)⁺=446 m/z.
[alpha]$_D$= +29.6 (DMSO).
IR (KBr) CO, cm⁻¹: 1630, 1680, 1710.
NMR(DMSO) delta: 0.81 (m) 6H, 1.10(m) 2H, 1.18 (m) 2H, 1.55 (m) 2H, 2.08 (m) 1H, 2.23 (m) 1H, 3.71 (m) 2H, 3.95 (m) 2H, 4.42 (m) 1H, 8.02 (d) 1H, 8.25 (m) 2H, 8.57 (s) 1H, 8.95 (m) 1H.

EXAMPLE 26p mp.=204°-206° C.
MS (m+1)⁺=432 m/z.
[alpha]$_D$= +18 (DMSO).
IR (KBr) CO, cm⁻¹: 1630, 1680, 1710.
NMR(DMSO) delta: 0 85 (m) 3H, 1.10 (m) 2H, 1.18 (m) 2H, 1.30 (m) 2H, 1.70 (m) 2H, 2.00 (m) 1H, 2.20 (m) 1H, 3.70 (m) 2H, 3.91 (m; 2H, 4.42 (m) 1H, 8.01 (d) 1H, 8.21 (m) 2H, 8.59 (s) 1H, 8.96 (m) 1H.

EXAMPLE 26r mp.=175°-177° C.
MS (m+1)⁺=449 m/z.
[alpha]$_D$= +8.9 (MeOH).
IR (KBr) CO, cm⁻¹: 1625, 1680, 1730.
NMR(DMSO) delta: 0.82, 0.90 (m) 3H, 1.17 (m) 3H, 1.30 (m) 2H, 1.70 (m) 2H, 1.95 (m) 1H, 2.15 (m) 1H, 3.58 (m) 1H, 3.75 (m) 2H, 3.95 (m) 2H, 4.10 (m) 1H, 4.37 (m) 1H, 7.73 (d) 1H, 8.30 (m) 2H, 8.62 (s) 1H, 9.00 (m) 1H.

EXAMPLE 26s mp.=185°-187° C.
MS (m+1)⁺=421 m/z.
[alpha]$_D$= +14.3 (MeOH).
IR (KBr) CO, cm⁻¹: 1625, 1680, 1730.
NMR(DMSO) delta: 1.17 (m) 3H, 1.36 (m) 3H, 1.95 (m) 2H, 2.15 (m) 2H, 3.55 (m) 2H, 3.80 (m) 2H, 3.95 (m) 2H, 4.10 (m) 1H, 4.35 (m) 2H, 7.73 (d) 1H, 8.22 (m) 2H, 8.63 (s) 1H, 8.90 (m) 1H.

EXAMPLE 26ff mp. = 190°-192° C.
MS (m+1)+ = 420 m/z.
[alpha]$_D$= +5.9 (MeOH).
IR (KBr) CO, cm$^{-1}$: 1630, 1680, 1720.
NMR(CDCl$_3$) delta: 1.91 (m) 5H, 2.13 (m) 2H, 2.32 (m) 1H, 3.47 (m) 6H, 3.65 (m) 3H, 4.30 (m) 1H, 4.48 (m) 2H, 5.10 (m) 3H, 7.10 (m) 3H, 7.32 (m) 5H, 7.94 (m) 1H, 8.51 (m) 1H.

EXAMPLE 26jj mp = 205° C. (dec.).
MS (m+1)+ = 608 m/z.
[alpha]$_D$= +35.9 (CH$_3$OH).
IR (KBr) CO, cm$^{-1}$: 1630, 1670, 1720.
NMR (DMSO) delta: 1.60 (m) 1H, 1.75 (m) 1H, 2 84 (m) 2H, 4.23 (m) 1H, 4.52 (m) 1H, 5.75 (m) 1H, 7.17 (m) 4H, 7.48 (m) 1H, 7.77 (m) 1H, 7.90 (m) 1H, 8.03 (m) 2H, 8.75 (m) 1H.

EXAMPLE 27

Using the process as described in Example 2a and substituting Pro for the solubilizing group A yields the protected Proline compound (I) (R$_1$=2,4 difluorophenyl, X=N, R$_2$=R$_3$=R$_4$=H, A=carbobenzyloxy Pro).
mp. = 217°-218° C.
[alpha]$_D$= -27.8° (CHCl$_3$)
IR (CDCl$_3$) CO,cm$^{-1}$: 1630, 1680, 1720.
NMR (CDCl$_3$) delta: 1.91 (m) 5H, 2.13 (m) 2H, 2.32 (m) 1H, 3.47 (m) 6H, 3.65 (m) 3H, 4.30 (m) 1H, 4.48 (m) 2H, 5.10 (m) 3H, 7.10 (m) 3H, 7.32 (m) 5H, 7.94 (m) 1H, 8.51 (m) 1H.

EXAMPLE 28

Using the process as described in Example 2b with the compound of Example 27 yields the deblocked Pro(HCl) salt (I) (R$_1$=2,4 difluorophenyl, X=N, R$_2$=R$_3$=R$_4$=H, A=Pro). mp.=203° C. (dec.).
MS (m+1)+ = 502 m/z.
[alpha]$_D$= 18.3 (CH$_3$OH).
IR (KBr) CO, cm$^{-1}$: 1630, 1677, 1730.
NMR(DMSO) delta: 1.85 (m) 4H, 2.07 (m) 1H, 2.25 (m) 1H, 3.20 (m) 4H, 4.10 (m) 1H, 4.32 (m) 1H, 7.35 (m) 1H, 7.61 (m) 1H, 7.80 (m) 1H, 8.10 (d) 1H, 8.52 (m) 1H, 8.82 (s) 1H, 8.89 (m) 1H, 9.82 (m) 1H.

EXAMPLE 29

Using the process as described in 2a and substituting Gly-Gly-Nval for the solubilizing group A yields the protected Gly-Gly Nval compound (I) (R$_1$=2,4-difluorophen-yl, X=N, R$_2$=R$_3$=R$_4$=H, A=Carbobenzyloxy Gly Gly Nval).
MS (m+1)+ = 7.52 m/z, mp.=118°-120° C.
[Alpha]$_D$= +8.0 (DMSO).
IR (KBr) CO, cm$^{-1}$: 1630,.1670, 1725.
NMR(CDCl$_3$) delta: 0.90 (m) 3H, 1.35 (m) 3H, 1.95 (m) 3H, 3.70 (m) 2H, 3.80 (m) 2H, 3.95 (m) 2H, 4.43 (m) 2H, 5.05 (m) 2H, 5.50 (m) 1H, 6.86 (m) 2H, 7.05 (m) 2H, 7.35 (m) 5H, 7.95 (d) 1H, 8.55 (s) 1H.

EXAMPLE 30

Using the process as described in 2b with the compound of Example 29 yields the deblocked Gly-Gly-Nval (HCl) salt (I) (R$_1$=2,4 difluorophenyl, x=n, R$_2$=R$_3$=R$_4$=H, A=Gly Gly-Nval). mp.=212° C. (dec.).
MS (m+1)+ = =618 m/z [Alpha]$_D$= +7.1 (DMSO).
IR (KBr) CO, cm$^{-1}$: 1635, 1670, 1730.
NMR(DMSO) delta: 0.83 (m) 3H, 1.21 (m) 2H, 1.50 (m) 2H, 1.80 (m) 1H, 2.03 (m) 1H, 3.68 (s) 2H, 3.83 (d) 2H, 4.21 (m) 2H, 7.34 (m) 1H, 7.59 (m) 1H, 7.80 (m) 1H, 8.10 (m) 2H B.15 (m) 1H. B.32 (m) 1H. 8.60 (m) 1H 8.82 (s) 1H.

EXAMPLE 31

7-[3 L-Methioninesulfone Amino-1-Pyrrolidinyl]-1-(2,4-Difluorophenyl)-6-Fluoro-1,4-Dihydro-4-Oxo 1,8-Naphthyridine 3-Carboxylic Acid Hydrochloride.

a) To a cold solution of 7-(3-amino-1 pyrrolidin-vl)-1-(2,4-difluorophenyl)-6-fluoro 1,4-dihydro 4-oxo-1,8 naphthyridine-3-carboxylic acid tosylate (4.50g) in dry DMF (90 ml) is added N-t-Boc-L-methionine-p-nitrophenyl ester (3.47g) followed by N-methylmorpholine (1.74g). The mixture is stirred in the cold for an additional hour, then at room temperature for about 17-18 hours. The resulting solution is poured into 500 ml of 0.5N HCl, and the mixture is extracted with 2×250 ml portion of CHCl$_3$. The combined extracts are washed with 5% NaHCO$_3$ solution and the organic phase is dried over MgSO$_4$ and evaporated to leave a solution of DMF and product. The residual DMF is removed by co-distillation with toluene, with ethylene dichloride, with CHCl$_3$ and CH$_2$Cl$_2$ to leave 5.06 grams of a light yellow colored foam. Trituration with ether caused the foam to crystallize and yield 4.43 grams of 7-(3-N-t-BOC-L-methionine-amino-1-pyrrolidinyl)-1-(2,4-difluorophenyl)-6-fluoro-1,4-dihydro-4-oxo-1,8-naphthyridine-3-carboxylic acid (I) (R$_1$=2,4-difluorophenyl, X=N, R$_2$=R$_3$=R$_4$=H, A=t-Boc-Met).

mp=214° C. (dec), [alpha]$_D$= -4.9 (CHCl$_3$)
IR (CDCl$_3$) CO, cm$^{-1}$: 1630, 1673, 1717
NMR(CDCl$_3$) delta: 1.40 (s) 9H, 1.90 (m) 2H, 2.10 (2-s) 3H, 2.53 (m) 2H, 4.23 (m) 1H, 4.53 (m) 1H, 5.22 (m) 1H, 7.05 (m) 3H, 7.94 (m) 1H, 8.48 (m) 1H.

b) To a cold solution of 7-(3-N-t-butoxycarbonyl-L-methionine-amino-1-pyrrolidinyl)-1-(2,4-difluorophenyl)-6-fluoro-1,4-dihydro-4-oxo-1,8-naphthyridine-3-Carboxylic Acid (2.16 g) in CH$_2$Cl$_2$ (50 ml) is added m-chloroperbenzoic acid (1.75g). This solution is stirred in the cold for an additional hour, then at room temperature of 17-18 hours. To the solution is added 1 ml of cyclohexene and stirred at room temperature for an hour. The reaction is diluted with CHCl$_3$ and washed with 3×250 ml portions of 5% NaHCO$_3$ solution. The organic phase is dried over MgSO$_4$ and evaporated to leave 2.04g of a tan colored foam. Trituration with ether caused the foam to crystallize and yield 1.86 grams of 7-(3-N-t-Boc-L-methionine-sulfone-amino-1-pyrrolidinyl]-1-(2,4-difluorophenyl)-6-fluoro-1,4-dihydro-4-oxo-1,8-naphthyridine-3-carboxylic acid (I) (R$_1$=2,4-difluorophenyl, X=N, R$_2$=R$_3$=R$_4$=H, A=-t—BOC—NH—CH(CH$_2$CH$_2$—SO$_2$CH$_3$) CO)

mp. = 160° C. (dec), (m+1)+ = 668 m/z, [Alpha]$_D$= +13.8 (CHCl$_3$)
IR (CDCl$_3$) CO, cm$^{-1}$: 1630, 1680, 1710.
NMR(CDCl$_3$) delta: 1.40 (s) 9H, 2.10 (m) 3H, 2.40 (m) 2H, 2.90 (2 s) 3H, 3.10 (m) 4H, 3.35 (m) 2H, 4.00 (m) 2H, 4.35 (m) 2H, 4.55 (m) 2H, 5.50 (m) 2H, 7.05 (m) 2H, 7.90 (m) 2H, 8.38 (m) 1H, 8.43 (s) 1H.

c) A solution of 7 (3-N-t-butoxy carbonyl L-methionine sulfone amino 1 pyrrolidinyl]-1 (2,4-difluoro phenyl)-6-fluoro-1,4-dihydro-4-oxo-1,8-naphthyridine-3-carboxylic acid (1.81g) in IM HCl in HOAc (20 ml) is stirred at room temperature for two hours. This solution is diluted with EtOH and evaporated to leave a yellow colored syrup. The residual HCl and HOAC is removed by co distillation with Etoh to leave 1.60 grams of a yellow colored solid, 7-(3-L-methionine sulfone-amino-1-pyrrolidinyl)-1-(2,4-difluorophenyl)-6-fluoro-1,4-dihydro-4-oxo-1,8-naphthyridine-3-carboxylic acid hydrochloride (I) ($R_1$=2,4 difluorophenyl, X=N, $R_2$=$R_3$=$R_4$=H, A=$NH_2$-CH($CH_2CH_2SO_2CH_3$)CO).

mp.=185° C. (dec), $(m+1)^+$=568 m/z, [Alpha]$_D$=+5.3 (MeOH), IR (KBr) CO, cm$^{-1}$: 1630, 1675, 1720.

NMR(DMSO) delta: 1.90 (m) 1H, 2.15 (m) 3H, 3.00 (2 s) 3H, 3.15 (m) 2H, 3.37 (m) 2H, 4.33 (m) 1H, 7.35 (m) 1H, 7.60 (m) 1H, 7.80 (m) 1H, 8.10 (d) 1H, 8.40 (m) 2H, 8.83 (s) 1H, 9.00 (m) 1H.

EXAMPLE 32

Using the process as described in Example 31a and replacing
7-(3-amino-1-pyrrolidinyl)-1-(2,4-difluorophenyl)-6-fluoro 1.4-dihydro-4-oxo-1,8-naphthyridine-3-carboxylic acid with 7-(3-amino-1-pyrrolidinyl)-1-cyclopropyl-6-fluoro-1,4-dihydro-4-oxoquinoline-3-carboxylic acid one obtains 7-(3-N-t-Boc-L-methionine-amino-1-pyrrolidinyl)-1-cyclopropyl-6-fluoro-1,4-dihydro-4-oxoquinoline-3-carboxylic acid (I) ($R_1$=cyclopropyl, X=CH, $R_2$=$R_3$=$R_4$=H, A=t-Boc-Met). mp.=198° C. (dec), MS $(m+1)^+$=563 m/z, [Alpha]$_D$=+8.0 (CHCl$_3$), IR (CDCl$_3$) CO, cm$^{-1}$: 1625, 1665, 1710.

NMR(CDCl$_3$) delta: 0.96 (m) 1H, 1.35 (m) 1H, 1.40 (2-s) 9H, 1.95 (m) 1H, 2.10 (2 s) 3H, 2.20 (m) 1H, 2.54 (m) 4H, 3.48 (m) 1H, 3.65 (m) 1H, 3.94 (m) 2H, 4.35 (m) 1H, 4.65 (m) 1H, 5.44 (m) 1H, 6.75 (2-d) 1H, 7.66 (2-d) 1H, 8.08 (2 s) 1H, 8.20 (m) 1H.

EXAMPLE 33

Using the process as described in Example 31c, the product of Example 32 yields 7-(3-L-methionine-amino-1-pyrrolidinyl)-1-cyclopropyl-6-fluoro-1,4-dihydro-4-oxoquinoline-3-carboxylic acid hydrochloride (I) ($R_1$=cyclopropyl, X=CH, $R_2$=$R_3$=$R_4$=H, A=-Met). mp.=185°-186° C., MS $(m+1)^+$=463 m/z, [Alpha]$_D$=+2.3 (DMSO)

IR (KBr) CO, cm$^{-1}$: 1625, 1680, 1710.

NMR(DMSO) delta: 1.15 (m) 2H, 1.30 (m) 2H, 1.95, 2.08 (2-s) 3H, 2.00 (m) 3H, 2.25 (m) 1H, 3.55 (m) 1H, 3.75 (m) 4H, 3.85 (m) 3H, 4.45 (m) 1H, 7.06 (d) 1H, 7.82 (d) 1H, 8.35 (m) 2H, 8.58 (s) 1H, 9.05 (m) 1H.

EXAMPLE 34

Using the process as described in Example 31b, the product of Example 32 yields 7 (3-L-methionine sulfone-amino-1-pyrrolidinyl)-1-cyclopropyl-6-fluoro-1,4-dihydro-4-oxo-quinoline-3-carboxylic acid (I) ($R_1$=cyclopropyl, X=CH, $R_2$=$R_3$=$R_4$=H, A=t-Boc-NH-CH($CH_2CH_2SO_2CH_3$)CO). mp.=156°-8° C., MS $(m+1)^+$=595 m/z, [alpha]$_D$=+20 (CHCl$_3$) delta: 1.41 (s) 9H, 2.22 (m) 3H, 2.43 (m) 2H, 2.90 (2 s) 3H, 3.11 (m) 2H, 3.48 (m) 1H, 3.65 (m) 2H, 3 95 (m) 2H, 4.40 (m) 1H, 4.60 (m) 1H, 5.58 (m) 1H, 6.77 (d) 1H, 7.66 (m) 1H, 8.05 (2 s) 1H, 8.40 (m) 1H.

EXAMPLE 35

Using the process as described in Example 31c, the product of Example 34 yields 7-(3-L-methionine sulfone-amino-1-pyrrolidinyl)-1-cyclopropyl-6-fluoro-1,4-dihydro-4-oxoquinoline-3-carboxylic acid hydrochloride (I) ($R_1$=cyclopropyl, X=CH, $R_2$=$R_3$=$R_4$=H, A=$NH_2$ CH ($CH_2CH_2SO_2CH_3$)CO).

EXAMPLE 36

Using the process as described in Example 31a and replacing 7-(3-amino-1-pyrrolidinyl)-1-(2,4-difluorophenyl)-6-fluoro-1,4-dihydro-4-oxo-1,8-naphthyridine-3-carboxylic acid with 7-(3-amino-1-pyrrolidinyl)-1-cyclopropyl-6,8-difluoro-1,4-dihydro-4-oxoquinoline-3-carboxylic acid one obtains 7-(3-N-t-Boc-L-methionine-amino-1-pyrrolidinyl)-1-cyclopropyl-6,8-difluoro-1,4-dihydro-4-oxoquinoline-3-carboxylic acid (I) ($R_1$=cyclopropyl, X=CF, $R_2$=$R_3$=$R_4$=H, A=t-Boc-Met). mp.=104°-105° C., MS $(m+1)^+$=581 m/z, [Alp=+12 (CHCl$_3$) IR (KBr) CO, cm$^{-1}$: 1620, 1670, 1710

NMR (CDCl$_3$) delta: 1.25 (m) 7H, 1.42 (s) 9H, 1.98 (m) 2H, 2.12 (2 s) 3H, 2.55 (m) 2H, 3.75 (m) 2H, 4.00 (m) 4H, 4.33 (m) 2H, 4.55 (m) 2H, 5.40 (m) 1H, 7.65 (m) 2H, 8.32 (2-s) 1H.

EXAMPLE 37

Using the process as described in Example 31c, the product of Example 36 yields 7-(3-L-methionine-amino-1-pyrrolidinyl)-1-cyclopropyl-6,8-difluoro-4-oxoquinoline-3-carboxylic acid hydrochloride (I) ($R_1$=cyclopropyl, X=CF, $R_2$=$R_3$=$R_4$=H, A=Met).

EXAMPLE 38

Using the process as described in Example 31b, the product of Example 36 yields 7 (3 L-methionine sulfone-amino-1-pyrrolidinyl) 1-cyclopropyl 6,8-difluoro-1,4-dihydro-4-oxo-quinoline-3-carboxylic acid (I) ($R_1$=cyclopropyl, X=CF, $R_2$=$R_3$=$R_4$=H, A=-t—Boc—NH—CH($CH_2CH_2$—$SO_2CH_3$)CO).

EXAMPLE 39

Using the process as described in Example 31c, the product of Example 38 yields 7-(3-L-methionine sulfone-amino-1-pyrrolidinyl)-1-cyclopropyl-6,8-difluoro-1,4-dihydro-4-oxoquinoline-3-carboxylic acid hydrochloride (I) ($R_1$=cyclopropyl, X=CF, $R_2$=$R_3$=$R_4$=H, A=$NH_2$CH($CH_2CH_2$-$SO_2CH_3$)CO).

EXAMPLE 40

Using the process as described in Example 31a, replacing N t Boc L-methionine p nitrophenyl ester with N-t-Boc-L-Asparagine-p-nitrophenyl ester, one can obtain 7-(3-N-t-Boc-L-Asparagine-amino-1-pyrrolidinyl)-1-(2,4-difluorophenyl)-6-fluoro-1,4-dihydro-4-oxo-1,8-naphthyridine-3-carboxylic acid (I) ($R_1$=2,4-difluorophenyl, X=N, $R_2$=$R_3$=$R_4$=H, A=t-Boc-Asn). mp.=147° (dec), $(m+1)^+$=619 m/z, [Alpha]$_D$=+6.0 (MeOH), IR (CDCl$_3$) CO, cm$^{-1}$: 1630, 1680, 1720.

NMR (CDCl$_3$) delta: 1.40 (s) 9H, 1.95 (m) 2H, 2.15 (m) 2H, 2.56 (m) 2H, 2.90 (m) 2H, 4.45 (m) 4H, 5.45 (m) 1H, 5.90 (m) 1H, 6.05 (m) 1H, 7.10 (m) 2H, 7.47 (m) 1H, 8.00 (d) 1H, 8.60 (m) 1H.

EXAMPLE 41

Using the process as described in Example 31c, the product of Example 40 yields 7-(3-L-Asparagine-amino-1-pyrrolidinyl)-1-(2,4-6-fluoro-1,4-dihydro-4-oxo-1,8-difluorophenyl)-3-carboxylic acid hydrochloride (I) ($R_1$=2,4 difluorophenyl, X=N, $R_2$=$R_3$=$R_4$=H, A=Asn). mp.=207° (dec), $(m+1)^+$==519 m/z, [Alpha]$_D$= −9.4 (MeOH) IR (KBr) CO, cm$^{-1}$: 1635, 1680, 1720.

NMR (DMSO) delta: 1.83 (m) 1H, 2.05 (m) 1H, 2.63 (m) 2H, 3.95 (m) 2H, 4.30 (m) 2H, 7.20 (m) 1H, 7.35 (m) 1H, 7.63 (m) 1H, 7.80 (m) 1H, 8.09 (d) 1H, 8.17 (m) 2H, 8.78 (m) 1H, 8.82 (s) 1H.

EXAMPLE 42

Using the process as described in Example 40, replacing
7-(3-amino-1-pyrrolidinyl)-1-(2,4-difluorophenyl)-6-fluoro -1,4-dihydro-4-oxo-1,8-naphthyridine-3-carboxylic acid with 7-(3-amino-1-pyrrolidinyl)-1-cyclopropyl-6,8-difluoro-1,4-dihydro-4-oxoquinoline-3-carboxylic acid, one obtains 7-(3-N-t-Boc-L-Asparagine-amino-1-pyrrolidinyl)-2-cyclopropyl-6,8-difluoro-1,4-dihydro-4-oxo-quinoline-3-carboxylic acid (I) ($R_1$=cyclopropyl X=CF, $R_2$=$R_3$=$R_4$=H, A=t-Boc-Asn). mp.=148°–150° C. (m+1)$^+$=564 m/z, [Alpha]$_D$=21.3 (DMSO) IR (KBr) CO, cm$^{-1}$: 1625, 1680, 1720.

NMR (DMSO) delta: 1.15 (m) 5H, 1.36 (2 s) 9H, 1.90 (m) 1H, 2.08 (m) 1H, 2.38 (m) 2H, 3.53 (m) 1H, 3.75 (m) 1H, 3.90 (m) 2H, 4.09 (m) 1H, 4.20 (m) 1H, 4.31 (m) 1H, 6.85 (m) 2H, 7.25 (m) 1H, 7.72 (d) 1H, 8.12 (m) 1H, 8.61 (s) 1H.

EXAMPLE 43

Using the process as described in Example 31c, the product of Example 42 yields 7-(3-L-Asparagine-amino-1-pyrrolidinyl)-1-cyclopropyl-6,8-difluoro-1,4-dihydro-4-oxoquinoline-3carboxylic acid hydrochloride (I). ($R_1$=cyclopropyl, X=CF, $R_2$=$R_3$=$R_4$=H, A=Asn). IR (KBr) CO, cm$^{-1}$: 1628, 1680, 1720.

NMR (DMSO) delta: 1.18 (m) 4H, 1.92 (m) 1H, 2.13 (m) 1H, 2.68 (m) 2H, 3.55 (m) 1H, 3.77 (m) 1H, 4.03 (m) 4H, 4.36 (m) 1H, 7.22 (d) 1H, 7.72 (m) 2H, 8.23 (m) 2H, 8.62 (s) 1H, 8.92 (d) 1H.

EXAMPLE 44

7-[3-L-Histidine-Amino-1-Pyrrolidinyl)-1-(2,4-Difluorophenyl)-6-Fluoro-1,4-Dihydro-4-oxo-1,8-Naphthyridine-3-Carboxylic Acid Dihydrochloride a) To a cold solution of
7-(3-amino-1-pyrrolidinyl)
1-(2,4-difluorophenyl)-6-fluoro 1,4 dihydro-4-oxo-1,8-naphthyridine-3-carboxylic acid tosylate (5.05g) in dry DMF (75 ml) is added N-t-butoxycarbonyl-N-pi-benzyloxymethyl-L-histidine N-hydroxyphthalimide ester (5.46g) followed by N-methylmorpholine (3.19g). The mixture is stirred in the cold for an additional hour, then at room temperature for 17–18 hours. The resulting solution is poured into 500 ml of 5% NaHCO$_3$ solution and the mixture is extracted with 2×250 ml portion of CHCl$_3$. The combined extracts are dried over MgSO$_4$ and evaporated to leave a solution of DMF and product. The residual DMF is removed by co distillation with toluene, with ethylene dichloride, CHCl$_3$ and CH$_2$Cl$_2$ to leave 5.15 g of a yellow colored foam. Trituration with ether caused the foam to crystallize and yield 3.28 grams 7-[3(N-2-t-Boc-N-pi-benzyl oxymethyl-L-histidine-amino-1-pyrrolidinyl]-1-(2,4-difluorophenyl)-6-fluoro-1,4-dihydro4-oxo 1,8-naphthyridine-3-carboxylic acid.

b) To a solution of 7-[3 (N-gamma-t -butoxycarbonyl-N-pi-benzyloxymethyl-L-histidine-amino-1-pyrrolidinyl)]-1-(2,4-difluorophenyl)-6-fluoro-1,4-dihydro-4-oxo-1,8-naphthyridine-3-carboxylic acid (1.52g) in 1.0M HCl in HOAc (50 ml) is stirred at room temperature for 4 hours. This solution is evaporated to leave a residue which is co-distilled several times with IPA to leave 1.37 g of a light yellow colored solid, 7-[3-(N-pi-benzyloxymethyl-L-histidine-amino-1-pyrrolidinyl]-1-(2,4-difluorophenyl)-6-fluoro 1,4-dihydro-4-oxo-1,8-naphthyridine-3-carboxylic acid. MS (m+1)$^+$=662 m/z IR (KBr) CO cm$^{-1}$: 1630, 1685, 1720

NMR (DMSO) delta: 1.77 (m) 1H, 2.05 (m) 1H, 4.14 (m) 1H, 4.30 (m) 1H, 4.60 (d) 1H, 5.77 (m) 1H, 7.30 (m) 5H, 7.58 (m) 1H, 7.80 (m) 1H, 8.08 (m) 1H, 8.57 (m) 2H, 8.83 (s) 1H, 9.32 (m) 1H.

c) A mixture of 7 [3-N-pi-benzyloxymethyl-L-histidine-amino-1-pyrrolidinyl)]-1-(2,4-difluorophenyl)6-fluoro-1,4-dihydro-4-oxo-1,8-naphthyridine-3-carboxylic acid (1.74g) 10% Pd/c (0.87g) and 100 ml acetic acid is reacted on a Parr Shaker apparatus under 60 psi of hydrogen atmosphere for 24 hours. After the reaction is completed, the hydrogen is vented, the catalyst is removed by filtration and the catalyst mixture is washed thoroughly. The filtrate is evaporated to leave a residue. The residual acetic acid is removed by co-distillation with ethanol and with CH$_3$OH to leave 1.68 grams of a yellow colored foam, 7 (3-L-histidine-amino-1-pyrrolidinyl)-1-(2,4-difluorophenyl)-6-fluoro-1,4-dihydro-4-oxo-1,8-naphthyridine-3-carboxylic acid hydrochloride (I) ($R_1$=2,4-difluorophenyl, X=N, $R_2$=$R_3$=$R_4$=H, A=histidine). [Alpha]$_D$= +13.6 (CH$_3$OH)

NMR (DMSO) delta: 1.30 (s) 9H, 1.87 (s) 3H, 1.95 (m) 1H, 2.72 (m) 1H, 2.85 (m) 1H, 4.23 (m) 1H, 4.40 (d).1H, 5.38 (m) 1H, 6.70 (m) 1H, 6.80 (m) 1H, 7.00 (m) 1H, 7.30 (m) 2H, 7.45 (m) 1H, 7.55 (m) 1H, 7.75 (m) 1H, 8.00 (m) 1H, 8.12 (m) 1H, 8.32 (s) 1H, 8.70 (m) 1H.

EXAMPLE 45

Using the process as described in Example 44, replacing N-2-t-BOC-N-pi-benzyloxymethyl-L-histidine-N-hydroxyphthalimide ester with N-t-BOC-L-Aspartic acid-b-benzyl-N-hydrosuccinimide ester, one obtains 7-(3-L-Asp-amino-1-pyrrolidinyl)-1-(2,4-difluorophenyl)-6-fluoro-1,4-dihydro-4-oxo-1,8-naphthyridine-3-carboxylic acid hydrochloride (I) ($R_1$=2,4-difluorophenyl, X=N, $R_2$=$R_3$=$R_4$=H, A=Asp). mp.=186°–188° C. MS (m+1)$^+$=520 m/z, IR (KBr) CO, cm$^{-1}$: 1630, 1690, 1730

NMR (DMSO) delta: 1.85 (m) 2H, 2.03 (m) 2H, 2.80 (m) 2H, 3.96 (m) 1H, 4.32 (m) 1H, 7.34 (m) 1H, 7.59 (m) 1H, 7.80 (m) 1H, 8.09 (d) 1H, 8.31 (m) 2H, 8.82 (s) 1H.

EXAMPLE 46

Using the process as described in Example 2, replacing the N-carbobenzyloxy-L-Norvaline-N-hydroxyphthalimide ester with N,N-dicarbobenzyloxy-L-lysine-N-hydroxysuccinimide ester, one obtains 7-(3-Lys-amino-1-pyrrolidinyl)-1-(2,4-difluorophenyl)-6-fluoro-1,4-dihydro-4-oxo-1,8-naphthyridine-3-carboxylic acid dihydrochloride (I) ($R_1$=2,4-difluorophenyl, X=N, $R_2$=$R_3$=$R_4$=H, A=Lys). mp.=198°–200° C.

MS (m+1)$^+$=533 m/z

[Alpha]$_D$= +3.9 (CH$_3$OH)

IR (KBr) CO, cm$^{-1}$: 1630, 1680, 1718

NMR (DMSO) delta: 1.35 (m) 2H, 1.56 (m) 2H, 1.72 (m) 2H, 2.08 (m) 1H, 2.73 (m) 2H, 3.70 (m) 1H, 4.32 (m) 1H, 7.35 (m) 1H, 7.60 (m) 1H, 7.82 (m) 1H, 8.08 (d) 1H, 8.81 (s) 1H, 9.03 (m) 1H.

EXAMPLE 47

Using the process described in Example 40, replacing 7-(3-amino-1-pyrrolidinyl)-6-fluoro-1-(2,4-difluorophenyl) -1,4-dihydro-4-oxo-1,8-naphthyridine-3-carboxylic acid with 7-(3-amino-1-pyrrolidinyl)-6-fluoro-1-(2,4-difluorophenyl) -1,4-dihydro-4-oxoquinoline 3-carboxylic acid, one obtains the 7-(3-N-t-Boc-L-Asparagine-amino-1-pyrrolidinyl)-6-fluoro-1-(2,4-difluorophenyl)-1,4-dihydro-4-oxoquinoline-3-carboxy lic acid (I) ($R$, =2,4-difluorophenyl, X=CH, $R_2=R_3=R_4=H$, A=t-B-amino-1-pyrrolidinyl)-1,4-dihydro-4-oxo naphthyridine-3-carboxylic acid, 1-ethyl-6-fluoro-7-(2-methyl-4-amino 1-pyrrolidinyl)-1,4-dihydro-4-oxo-quinoline-3-carboxylic acid, 1-ethyl-6-fluoro-7-(2-methyl-4-amino-1-pyrrolidinyl)-1,4-dihydro-4-oxo-1,8-naphthyridine-3-carboxylic acid, 1-cyclopropyl-7-(2-methyl-4-amino-1-pyrrolidinyl)-6,8-difluoro-1,4-dihydro-4-oxoquinoline-3-carboxylic acid, 1-cyclopropyl-7(2-methyl-4-amino-1-pyrrolidinyl)-6-fluoro-8-chloro-1,4-dihydro-4-oxo quinoline 3-carboxylic acid and substituting various amino acids or peptides for one solubilizing group A, one obtains the following compounds as shown in the Table III.

TABLE III

| | Starting Material | | Reactant | | Resultant Compound | |
|---|---|---|---|---|---|---|
| | X | $R_1$ | A | A | X | $R_1$ |
| a | N | 2,4-difluorophenyl | Nval | Nval | N | 2,4-difluorophenyl |
| b | N | 2,4-difluorophenyl | Leu | Leu | N | 2,4-difluorophenyl |
| c | N | 2,4-difluorophenyl | Ala | Ala | N | 2,4-difluorophenyl |
| d | CH | 2,4-difluorophenyl | Nval | Nval | CH | 2,4-difluorophenyl |
| e | N | 4-fluorophenyl | Nval | Nval | N | 4-fluorophenyl |
| f | CH | 4-fluorophenyl | Nval | Nval | CH | 4-fluorophenyl |
| g | N | cyclopropyl | Nval | Nval | N | cyclopropyl |
| h | N | cyclopropyl | Leu | Leu | N | cyclopropyl |
| i | CH | cyclopropyl | Nval | Nval | CH | cyclopropyl |
| j | CH | cyclopropyl | Ala | Ala | CH | cyclopropyl |
| k | CF | cyclopropyl | Nval | Nval | CF | cyclopropyl |
| l | CCl | cyclopropyl | Nval | Nval | CCl | cyclopropyl |
| m | N | ethyl | Nval | Nval | N | ethyl |
| n | CH | ethyl | Nval | Nval | CH | ethyl |

$Z = C_6H_5-CH_2-O-\overset{O}{\underset{\|}{C}}-$ c-Asn).

EXAMPLE 48

Using the process described in Example 41, the product of Example 47 yields 7-(3-L-Asparagine-amino-1-pyrrolidinyl-1-(2,4-difluorophenyl)-6-fluoro-1,4-dihydro-4-oxoquinoline-3-carboxylic acid hydrochloride (I). ($R_1$=2,4-difluorophenyl, X=CH, $R_2=R_3=R_4=H$, A=Asn).

EXAMPLE 49

Using the process as described in Example 24a, replacing 1-(2,4-difluorophenyl)-6-fluoro-7-(3-amino-1-pyrrolidinyl)-1,4-dihydro-4-oxo-quinoline-3-carboxylic acid with an appropriate quinolone and naphthyridine derivative such as 1-(2,4-difluorophenyl)-6-fluoro-7-(2-methyl-4-amino-1-pyrrolidinyl)-1,4-dihydro-4-oxoquinoline-3-carboxylic acid, 1-(2,4-difluorophenyl)-6-fluoro-7-(2-methyl-4-amino-1-pyrrolidinyl)-1,4-dihydro-4-oxo-1,8-naphthyridine-3-carboxylic acid, 1-(4-fluoro phenyl)-6-fluoro-7-(2-methyl-4-amino-1-pyrrolidinyl)-1,4-dihydro-4-oxo-quinoline-3-carboxylic acid, 1-(4-fluorophenyl)-6-fluoro-7-(2-methyl-4-amino-1-pyrrolidinyl)-1,4-dihydro-4-oxo-1,8-naphthyridine-3-carboxylic acid, 1-cyclopropyl-6-fluoro-7-(2-methyl-4-amino-1-pyrrolidinyl)-1,4-dihydro-4-oxoquinoline-3-carboxylic acid, 1-cyclopropyl-6-fluoro-7-(2-methyl-4-

EXAMPLE 50

Using the process as described in Example 24(b), the compounds of Example 49 (a-n) yield the following corresponding quinolone and naphthyridine derivatives (a-n) and their hydrochloride salts as shown in Table IV.

TABLE IV

| | A | X | $R_1$ |
|---|---|---|---|
| a | Nval | N | 2,4-difluorophenyl |
| b | Leu | N | 2,4-difluorophenyl |
| c | Ala | N | 2,4-difluorophenyl |
| d | Nval | CH | 2,4-difluorophenyl |
| e | Nval | N | 4-fluorophenyl |
| f | Nval | CH | 4-fluorophenyl |
| g | Nval | N | cyclopropyl |

TABLE IV-continued

[Structure: pyrrolidinyl-substituted naphthyridine/quinolone with F, CH3, A-NH, X, N-R1, and COOH groups]

| | A | X | R1 |
|---|---|---|---|
| h | Leu | N | cyclopropyl |
| i | Nval | CH | cyclopropyl |
| j | Ala | CH | cyclopropyl |
| k | Nval | CF | cyclopropyl |
| l | Nval | CCl | cyclopropyl |
| m | Nval | N | ethyl |
| n | Nval | CH | ethyl |

EXAMPLE 51

Using the process as described in either Example 1a or 3a and substituting Gly-Nval for the solubilizing group A, yields the protected Gly-Nval compound (I) ($R_1$ = 2,4-difluorophenyl, X=N, $R_2$=$R_4$=$R_3$=H, A = -carbobenzyloxy Gly Nval). MS (m+1)$^+$=695 m/z [alpha]$_D$= −11.2 (CDCl$_3$), mp=115°-117° C.

NMR data: (CDCl$_3$) delta: 0.90 (m) 3H, 1.30 (m) 3H, 1.65 (m) 3H, 1.85 (m) 1H, 2.03 (m) 2H, 3.30 (m) 2H, 3.85 (m) 4H, 4.57 (m) 4H, 5.05 (s) 2H, 5.52 (m) 1H, 6.62 (m) 1H, 7.10 (m) 4H, 7.32 (m) 6H, 7.85 (d) 1H, 8.43 (d) 1H.

IR data: (CDCl$_3$) CO, cm$^{-1}$: 1630, 1670, 1722.

EXAMPLE 52

Using the process as described in Example 3b with the compound of Example 51 yields the deblocked Gly-Nval (HCl) salt, (I) ($R_1$=2,4 difluorophenyl, X=N, $R_2$=$R_3$=$R_4$=H, A=Gly Nval). mp=180°-182° C., MS (m+1)$^+$=61 m/z, [alpha]$_D$=5.3° CH$_3$OH)

NMR Data: (DMSO) delta: 0.83 (m) 3H, 1.22 (m) 3H, 1.50 (m) 3H, 1.80 (m) 1H, 2.02 (m) 1H, 3.55 (s) 2H, 4.27 (m) 2H, 7.32 (m) 1H, 7.60 (m) 1H, 7.81 (m) 1H, 8.02 (m) 2H, 8.10 (d) 1H, 8.41 (m) 1H, 8.56 (d) 1H, 8.82 (s) 1H.

IR data: (KBr) CO, cm$^{-1}$: 1630, 1660, 1720.

EXAMPLE 53

Using the process as described in either Example 1a or 3a and substituting Gly-Gly for the solubilizing group A, yields the protected Gly-Gly compound (I) ($R_1$=2.4 difluorophenyl, X=N, $R_2$=$R_4$=$R_3$=H. A=-carbobenzyloxy Gly-Gly). MS (m+1)$^+$=653 m/z, mp=125°-128° C.

IR data: (CDCl$_3$) CO, cm$^{-1}$: 1630, 1672, 1722.

EXAMPLE 54

Using the process as described in Example 3b with the compound of Example 51 yields the deblocked Gly-Gly (HCl) salt, (I) ($R_1$=2,4-difluorophenyl, X=N, $R_2$=$R_3$=$R_4$=H, A=Gly-Gly). (m+1)$^+$519 m/z, mp=175°-178° C.

NMR data: (DMSO) delta: 1.82 (m) 1H, 2.04 (m) 1H, 3.34 (m) 2H, 3.60 (m) 2H, 3.77 (m) 2H, 4.30 (m) 1H, 7.35 (m) 1H, 7.60 (m) 1H, 7.80 (m) 1H, 8.05 (m) 3H, 8.31 (m) 1H, 8.60 (m) 1H, 8.83 (s) 1H, 15.17 (s) 1H.

IR data: (KBr) CO, cm$^{-1}$: 1635, 1670, 1720.

EXAMPLE 55

Using the process as described in either Example 1a or 3a and substituting Gly-Ala, Ala-Nval, Ala-Met, Ala-Leu, Leu-Nval, Leu-Leu, Leu-Met, Met-Met, Met-Leu, Met-Ala, Met-Nval, Nval-Gly, Nva-Ala, Gly-Gly-Gly, D-Ala-Ala, Gly-Nval-Nval, Gly-Gly-Ala, Gly-Ala-Ala, Phe-Ala, Leu-Ala, Val-Ala, Val-Leu, Gly-Gly-Gly-Gly, Gly-Gly-Gly Ala and Gly-Gly-Gly-Nval for the solubilizing qroup A and subjecting the products from these reactions with the same process as described in Example 3b, or following a similar procedure as Examples 31a and 31c, substituting the above group, one can obtain the hydrochloride salt of the following compounds.

a. 7-(3-Gly-Ala-amino-1-pyrrolidinyl)-6-fluoro-1(2,4-difluorophenyl)-1,4-dihydro-4-oxo-1,8-naphthyridine-3-carboxylic acid;

b. 7-(3-Ala-Nval-amino-1-pyrrolidinyl)-6-fluoro-1-(2,4-difluorophenyl)-1,4-dihydro-4-oxo-1,8-naphthyridine-3-carboxylic acid;

c. 7-(3-Leu-Nval-amino-1-pyrrolidinyl)-6-fluoro-1-(2,4-difluorophenyl)-1,4-dihydro-4-oxo-1,8-naphthyridine-3-carboxylic acid;

d. 7-(3-Met-Nval-amino-1-pyrrolidinyl)-6-fluoro-1-(2,4-difluorophenyl)-1,4-dihydro-4-oxo-1,8-naphthyridine-3-carboxylic acid;

e. 7-(3-Nval-Gly-amino-1-pyrrolidinyl)-6-fluoro-1-(2,4-difluorophenyl)-1,4-dihydro-4-oxo-1,8-naphthyridine-3-carboxylic acid;

f. 7-(3-Nval-Ala-amino-1-pyrrolidinyl)-6-fluoro-1-(2,4-difluorophenyl)-1,4-dihydro-4-oxo-1,8-naphthyridine-3-carboxylic acid;

g. 7-(3-Gly-Gly-Gly-amino-1-pyrrolidinyl)-6-fluoro-1-(2,4-difluorophenyl)-1,4-dihydro-4-oxo-1,8-naphthyridine-3-carboxylic acid;

h. 7-(3-Gly-Nval-Nval-amino-1-pyrrolidinyl)-6-fluoro-1-(2,4-difluorophenyl)-1,4-dihydro-4-oxo-1,8-naphthyridine-3-carboxylic acid;

i. 7-(3-Gly-Gly-Ala-amino-1-pyrrolidinyl)-6-fluoro 1-(2,4-difluorophenyl)-1,4-dihydro-4-oxo-1,8-naphthyridine-3-carboxylic acid;

j. 7-(3-Gly-Ala-Ala-amino-1-pyrrolidinyl)-6-fluoro-1-(2,4-difluorophenyl)-1,4-dihydro-4-oxo-1,8-naphthyridine-3-carboxylic acid;

k. 7-(3-Gly-Gly-Gly-Gly-amino-1-pyrrolidinyl)-6-fluoro-1-(2,4-difluorophenyl)-1,4-dihydro-4-oxo-1,8-naphthyridine-3-carboxylic acid;

l. 7-(3-Gly-Gly-Gly-Ala-amino-1-pyrrolidinyl)-6-fluoro-1-(2,4-difluorophenyl)-1,4-dihydro-4-oxo-1,8-naphthyridine-3-carboxylic acid;

m. 7-(3-Gly-Gly-Gly-Nval-amino-1-pyrrolidinyl)-6-fluoro-1-(2,4-difluorophenyl)-1,4-dihydro-4-oxo-1,8-naphthyridine-3-carboxylic acid;

n. 7(3-Ala-Met-amino-1-pyrrolidinyl)-6-fluoro-1-(2,4-difluorophenyl)-1,4-dihydro-4-oxo-1,8-naphthyridine-3-carboxylic acid;

o. 7-(3-Met-Met-amino-1-pyrrolidinyl)-6-fluoro-1-(2,4-difluorophenyl)-1,4-dihydro-4-oxo-1,8-naphthyridine-3-carboxylic acid;

p. 7-(3-Leu-Met-amino-1-pyrrolidinyl)-6-fluoro-1-(2,4-difluorophenyl)-1,4-dihydro-4-oxo-1,8-naphthyridine-3-carboxylic acid;

q. 7-(3-Leu-Leu-amino-1-pyrrolidinyl)-6-fluoro-1(2,4-difluorophenyl)-1,4-dihydro-4-oxo-1,8-naphthyridine-3-carboxylic acid;

r. 7-(3-Ala-Leu-amino-1-pyrrolidinyl)-6-fluoro-1-(2,4-difluorophenyl)-1,4-dihydro-4-oxo-1,8-naphthyridine-3-carboxylic acid;
s. 7-(3-,Met-Leu-amino-1-pyrrolidinyl)-6-fluoro-1-(2,4-difluorophenyl)-1,4-dihydro-4-oxo-1,8-naphthyridine-3-carboxylic acid;
t. 7-(3-Phe-Ala-amino-1-pyrrolidinyl)-6-fluoro-1(2,4-difluorophenyl)-1,4-dihydro-4-oxo-1,8-naphthyridine-3-carboxylic acid;
u. 7-(3-Leu-Ala-amino-1-pyrrolidinyl)-6-fluoro-1-(2,4-difluorophenyl)-1,4-dihydro-4-oxo-1,8-naphthyridine-3-carboxylic acid;
v. 7-(3-Met-Ala-amino-1-pyrrolidinyl)-6-fluoro-1- (2,4-difluorophenyl)-1,4-dihydro-4-oxo-1,8-naphthyridine-3-carboxylic acid;
w. 7-(3-Val-Ala-amino-1-pyrrolidinyl)-6-fluoro-1(2,4-difluorophenyl)-1,4-dihydro-4-oxo-1,8naphthyridine-3-carboxylic acid;
x. 7-(3-Val-Leu-amino-1-pyrrolidinyl)-6-fluoro-1(2,4-difluorophenyl)-1,4-dihydro-4-oxo-1,8-naphthyridine-3-carboxylic acid; and
y. 7-(3-D-Ala-L-Ala-amino-1-pyrrolidinyl)-6-fluoro-1-(2,4-difluorophenyl)-1,4-dihydro-4-oxo-1,8-naphthyridine-3-carboxylic acid.

TABLE V

The physical data for the hydrochloride salt of the products in the designated Examples is as follows:

EXAMPLE 55b mp=200°-202° C.
MS $(m+1)^+$ =575 m/z.
$[alpha]_D$= +10.2 ($CH_3OH$).
IR (KBr) CO, $cm^{-1}$: 1630, 1670, 1715.
NMR (DMSO $d_6$) delta: 0.80 (m) 3H, 1.25 (m) 5H, 1.47 (m) 2H, 1.78 (m) 1H, 2.00 (m) 1H, 3.80 (m) 2H, 4.18 (m) 2H, 7.30 (m) 1H, 7.53 (m) 1H, 7.75 (m) 1H, 8.05 (d) 1H, 8.34 (d) 1H, 8.47 (d) 1H, 8.77 (s) 1H.

EXAMPLE 55c mp=180°-182° C.
MS $(m+1)^+$617 m/z.
$[alpha]_D$= +19.0 ($CH_3OH$).
IR (KBr) CO, $cm^{-1}$: 1630, 1670, 1710.
NMR ($CD_3OD$) delta: 0.95 (m) 9H, 1.34 (m) 3H, 1 67 (m) 5H, 1.96 (m) 1H, 2.15 (m) 1H, 3 87 (m) 1H, 4.34 (m) 2H, 7.26 (m) 2H, 7.65 (m) 1H, 8.05 (m) 1H, 8.78 (s) 1H.

EXAMPLE 55d mp=170°-172° C.
MS $(m+1)^+$ =635 m/z.
$[alpha]_D$= +24.2 ($CH_3OH$).
IR (KBr) CO, $cm^{-1}$: 1630, 1670, 1720
NMR (DMSO-$d_6$) delta: 0.85 (m) 3H, 1.28 (m) 3H, 1.53 (m) 3H, 1.95 (m) 2H, 2.05 (m) 3H, 3.85 (m) 1H, 4.25 (m) 1H, 7.33 (m) 1H, 7.55 (m) 1H, 7.80 (m) 1H, 8.10 (m) 1H, 8.15 (m) 2H, 8.38 (m) 1H, 8.60 (m) 1H, 8.82 (s) 1H.

EXAMPLE 55f mp=195°-197° C.
MS $(m+1)^+$ =575 m/z.
$[alpha]_D$= +25.6 ($CH_3OH$)
IR (KBr) CO, $cm^{-1}$: 1630, 1670, 1720
NMR ($CD_3OD$) delta: 0.95 (m) 3H, 1.34 (m) 3H, 1.45 (m) 2H, 1.83 (m) 2H, 1.95 (m) 1H, 2.15 (m) 1H, 3.83 (m) 2H, 4.33 (m) 2H, 7.25 (m) 3H, 7.65 (m) 1H, 8.03 (m) 1H, 8.77 (m) 1H.

EXAMPLE 55n mp=185°-187° C.
MS $(m+1)^+$ =607 m/z.
$[alpha]_D$= +10.3 ($CH_3OH$),
IR (KBr) CO, $cm^{-1}$: 1630, 1670, 1725.
NMR ($CD_3OD$) delta: 1.48 (m) 3H, 2.02 (m) 6H, 2.15 (m) 1H, 2.50 (m) 2H, 3.95 (m) 1H, 4.40 (m) 2H, 7.28 (m) 2H, 7.68 (m) 1H 8.02 (m) 1H, 8.75 (s) 1H.

EXAMPLE 55o mp=163°-165° C.
$(m+1)^+$ =667 m/z.
$[alpha]_D$= +24.6 ($CH_3OH$).
IR (KBr) CO, $cm^{-1}$: 1630, 1670, 1720.
NMR ($CD_3OD$) delta: 2.10 (m) 11H, 2.55 (m) 4H, 3.95 (m) 1H, 4.40 (m) 2H, 7.28 (m) 2H, 7.65 (m) 1H, 8.05 (m) 1H, 8.77 (s) 1H.

EXAMPLE 55p mp=180°-183° C.
MS $(m+1)^+$ =649 m/z.
alpha$]_D$= +18.9 ($CH_3OH$) .
IR (KBr) CO, $cm^{-1}$: 1630, 1665, 1720.
NMR ($CD_3OD$) delta: 0.97 (m) 6H, 1.70 (m) 3H, 1.95 (m) 1H, 2.05 (m) 3H, 2.50 (m) 2H, 3.87 (m) 1H, 4.35 (m) 1H, 4.45 (m) 1H, 7.25 (m) 2H, 7.65 (m) 1H, 8.05 (m) 1H, 8.77 (s) 1H.

EXAMPLE 55q mp=194°-195° C.
MS $(m+1)^+$ =631 m/z.
$[alpha]_D$= +18.5 ($CH_3OH$.
IR (KBr) CO, $cm^{-1}$: 1630, 1675, 1725.
NMR ($CD_3OD$) delta: 0.95 (m) 12H, 1.63 (m) 7H, 1.94 (m) 1H, 2.15 (m) 1H, 3.85 (m) 1H, 4.37 (m) 2H, 7.25 (m) 2H, 7.65 (m) 1H, 8.05 (m) 1H, 8.77 (s) 1H.

EXAMPLE 55r mp=200°-202° C.
MS $(m+1)^+$ =589 m/z.
$[alpha]_D$ = +7.8 ($CH_3OH$).
IR (KBr) CO, $cm^{-1}$: 1630, 1670, 1720.
NMR ($CD_3OD$) delta: 0.90 (m) 6H, 1.45 (m) 3H, 1 58 (m) 3H, 1.95 (m) 1H, 2.13 (m) 1H, 3.29 (m) 2H, 3.90 (m) 1H, 4.34 (m) 2H, 7.25 (m) 2H, 7.65 (m) 1H, 8.03 (m) 1H, 8.75 (s) 1H.

EXAMPLE 55s mp=178°-180° C.
MS $(m+1)^+$ =649 m/z.
$[alpha]_D$ = +24.5 ($CH_3OH$).
IR (KBr) CO, $cm^{-1}$: 1630, 1670, 1715.
NMR ($CD_3OD$) delta: 0.90 (m) 6H, 1.55 (m) 3H, 1.92 (m) 1H, 2.10 (m) 4H, 2.55 (m) 2H, 3.29 (m) 2H, 3.95 (m) 1H, 4.35 (m) 2H, 7.25 (m) 2H, 7.65 (m) 1H, 8.03 (m) 1H, 8.75 (s) 1H.

EXAMPLE 55t mp=192°-194° C.
MS $(m+1)^+$ =623 m/z.
$[alpha]_D$= +20.8 ($CH_3OH$).
IR (KBr) CO, $cm^{-1}$: 1630, 1670, 1720.
NMR (CD OD) delta: 1.34 (m) 3H, 1.95 (m) 1H, 2.16 (m) 1H, 2.95 (m) 1H, 3.20 (m) 1H, 4.08 (m) 1H, 4.35 (m) 2H, 7.30 (m) 7H, 7.63 (m) 1H, 8.04 (m) 1H, 8.75 (m) 1H.

EXAMPLE 55u mp=197°-200° C.
MS (m+1)+ =589 m/z.
[alpha]$_D$= +25.0 (CH$_3$OH).
IR (KBr) CO,. cm$^{-1}$: 1630, 1660, 1720.
NMR (CD$_3$OD) delta: 0.98 (m) 6H, 1.34 (m) 3H, 1.70 (m) 3H, 1.95 (m) 1H,. 2.15 (m) 1H, 3.85 (m) 1H, 4.35 (m) 1H, 7.25 (m) 2H, 7.65 (m) 1H, 8.04 (m) 1H, 8.78 (s) 1H.

EXAMPLE 55v mp=178°-180° C.
MS (m+1)+ =607 m/z.
[alpha]$_D$= +31.8 (CH$_3$OH).
IR (KBr) CO, cm$^{-1}$: 1630, 1670, 1720.
NMR (CD$_3$OD) delta: 1.35 (m) 3H, 1.95 (m) 1H, 2.12 (m) 3H, 2.60 (m) 2H, 3.95 (m) 1H, 4.34 (m)2H, 7.27 (m) 2H, 7.66 (m) 1H, 8.05 (m) 1H, 8.78 (s) 1H.

EXAMPLE 55w mp=201°-204° C.
MS (m+1)+ =575 m/z.
[alpha]$_D$= +20.6 (CH$_3$OH).
IR (KBr) CO, cm$^{-1}$: 1630, 1665, 1720,
NMR (CD$_3$OD) delta: 1.03 (m) 6H, 1.35 (m) 3H, 1.95 (m) 1H, 2.18 (m) 1H, 3.65 (m) 1H, 4.34 (m) 1H, 7.25 (m) 2H, 7.65 (m) 1H, 8.05 (m) 1H, 8.76 (s) 1H.

EXAMPLE 55x mp=192°-195° C.
MS (m+1)+ =617 m/z.
[alpha]$_D$= +17.4 (CH$_3$OH).
IR (KBr) CO, cm$^{-1}$: 1630, 1670, 1720.
NMR (CD$_3$OD) delta: 0.95 (m) 12H, 1.55 (m) 2H, 1.95 (m) 1H, 2.18 (m) 1H, 3.65 (m) 1H, 4.35 (m) 1H, 7.25 (m) 2H, 7.65 (m) 1H, 8.05 (m) 1H, 8.78 (s) 1H.

EXAMPLE 55y mp=188°-190° C.
MS (M+1)+ =547 m/z.
[alpha]$_D$= +5.1 (CH$_3$OH).
IR (KBr) CO, cm$^{-1}$: 1630, 1670, 1710.
NMR (CD$_3$OD) delta: 1.33 (m) 3H, 1 48 (m) 3H, 1.95 (m) 1H, 2.15 (m) 1H, 3.95 (m) 1H, 4.28 (m) 1H, 4.36 (m) 1H, 7.27 (m) 2H, 7.65 (m) 1H, 8.05 (m) 1H, 8.32 (m) 1H, 8.78 (s) 1H.

Solubility

Some of the compounds of this invention show unexpected improvement in aqueous solubility especially when the N-1 position is substituted by a substituted phenyl group as shown in Table VI below where the compounds produced in Examples 1b, 2b, 3b, 5, 11, 13, 15, 17, 19, 21, 30, 31c, 41, 44c, and 45, having a 2,4 difluorophenyl substitution at the N-1 position, are compared to a parent compound which is tosufloxacin (i.e. 7 (3 amino 1-pyrrolidinyl)-6-fluoro,1-(2,4-difluorophenyl)-1,4-dihydro-4-oxo-1,8naphthyridine-3-carboxylic acid); Example 26i is compared to its parent compound A which is 7-(3-amino-1-pyrrolidinyl)-6-fluoro-1-(4-fluorophenyl)-1,4-dihydro-4-oxo-1,8-naphthyridine-3-carboxylic acid. Further, dipeptide or tripeptide derivatives are generally more soluble than an amino acid derivative (when the polypeptide is compared to any derivative having one amino acid residue included in the polypeptide) at the physioloqical pH (i.e., 7.4) which may help improve absorption. See, for example, 1b, 3b, 11, 15, 30 compared to 2b, 5, 17 and 52.

TABLE VI

| Example | A | Salt | Water Solubility mg/ml* | pH 7.4 mg/ml |
|---|---|---|---|---|
| tosufloxacin | H | Tosylate | 0.65 | 0.01 |
| 1b | Gly—Phe | HCl | >98 | 1.037 |
| 2b | Nval | HCl | >20 | 0.23 |
| 3b | Nval—Nval | HCl | >40 | 0.68 |
| 5 | Phe | HCl | >101 | 0.34 |
| 11 | Ala—Phe | HCl | >20 | 0.59 |
| 13 | Tyr | HCl | >90 | 0.06 |
| 15 | Ala—Ala | HCl | >70 | 1.07 |
| 17 | Ala | HCl | >20 | 0.12 |
| 19 | Val | HCl | >10 | 0.41 |
| 21 | Leu | HCl | >35 | 0.14 |
| A | H | HCl | 1.4 | 0.014 |
| 26i | Nval | HCl | >9 | 0.24 |
| 30 | Gly—Gly—Nval | HCl | >19 | 0.62 |
| 31c | Met—sulfone | HCl | >35 | 0.03 |
| 41 | Asn | HCl | >35 | 0.40 |
| 44c | His | HCl | >100 | 0.30 |
| 45 | Asp | HCl | 4.1 | 2.40 |
| 52 | Gly—Nval | HCl | 6.89 | 0.08 |
| 55b | Ala—Nval | HCl | 26 | 1.03 |
| 54 | Gly—Gly | HCl | 20 | 0.10 |
| 55n | Ala—Met | HCl | 20 | 2.50 |
| 55o | Met—Met | HCl | 22 | 0.31 |
| 55p | Leu—Met | HCl | 23 | 0.06 |
| 55q | Leu—Leu | HCl | 19 | 0.19 |
| 55r | Ala—Leu | HCl | 26 | 2.0 |

*the sign > refers to an approximate value and the solubility may be within 10% higher

In Vitro Antibacterial Activity

In Vitro Tests

The in vitro antibacterial activity of the test compounds was determined by conventional agar dilution procedures. The organisms were grown overnight in brain-heart infusion (BHI) broth (Difco 0037-01-6) at 36° C. Twofold dilutions of the stock solution (2000 mcg/mL) of the test compound were made in BHI agar to obtain a test concentration ranging from 200 to 0.005 mcg/mL. The plate was inoculated with approximately 10$^4$ organisms. It was then incubated at 36° C. for 18 h. The minimal inhibitory concentration (MIC) was the lowest concentration of the test compound that yielded no visible growth on the plate.

The results of in vitro testing of the compounds are shown in Table VII below where the growth medium for this study was Brain Heart Infusion Agar (BHIA), the parent compound is tosufloxacin. The MIC results are in μg/ml.

TABLE VII

| | | MIC (ug/ml) | | | | Tosu-floxacin |
|---|---|---|---|---|---|---|
| Organism | | 15 | 1b | 2b | 5 | |
| STAPHYLOCOCCUS AUREUS | ATCC 6538P | 1.56 | .1 | .05 | .2 | 0.02 |
| STAPHYLOCOCCUS AUREUS | CMX 686B | 6.2 | .1 | — | — | 0.05 |
| STAPHYLOCOCCUS AUREUS | A5177 | 12.5 | .2 | .2 | .78 | 0.05 |
| STAPHYLOCOCCUS AUREUS | 45 | 12.5 | .1 | .2 | 1.56 | 0.1 |
| STAPHYLOCOCCUS AUREUS | 45 RAR2 | 25 | .1 | .39 | .78 | 0.1 |
| STAPHYLOCOCCUS AUREUS | 642A | — | — | .2 | .39 | — |

TABLE VII-continued

| | | MIC (ug/ml) | | | | |
| --- | --- | --- | --- | --- | --- | --- |
| Organism | | 15 | 1b | 2b | 5 | Tosufloxacin |
| STAPHYLOCOCCUS AUREUS | NCTC 10649 | — | — | .1 | .39 | — |
| STAPHYLOCOCCUS AUREUS | CMX 503A | 12.5 | .1 | — | — | 0.05 |
| STAPHYLOCOCCUS AUREUS | CMX 553 | 12.5 | .2 | .39 | .78 | 0.1 |
| STAPHYLOCOCCUS EPIDERMIDIS | 3519 | 12.5 | .78 | .39 | .78 | 0.1 |
| MICROCOCCUS LUTEUS | ATCC 9341 | >100 | 6.25 | 25 | 25 | 1.56 |
| MICROCOCCUS LUTEUS | ATCC 4698 | 100 | .78 | 25 | 12.5 | 0.78 |
| ENTEROCOCCUS FAECIUM | ATCC 8043 | 50 | 1.56 | .78 | 3.1 | 0.2 |
| STREPTOCOCCUS BOVIS | A5169 | 50 | 1.56 | 1.56 | 6.2 | .39 |
| STREPTOCOCCUS AGALACTIAE | CMX 508 | 12.5 | 1.56 | 1.56 | 3.1 | .39 |
| STREPTOCOCCUS PYOGENES | EES61 | 12.5 | 1.56 | 1.56 | 3.1 | .2 |
| STREPTOCOCCUS PYOGENES | 930 CONST | 12.5 | .78 | .78 | 1.56 | .2 |
| STREPTOCOCCUS PYOGENES | 2548 INDUC | 12.5 | .78 | .39 | .78 | .1 |
| ESCHERICHIA COLI | JUHL | 12.5 | 3.12 | .78 | 3.1 | .02 |
| ESCHERICHIA COLI | SS | .39 | .2 | .02 | .1 | .005 |
| ESCHERICHIA COLI | DC-2 | 100 | 100 | 12.5 | 50 | .39 |
| ESCHERICHIA COLI | H560 | 6.2 | 1.56 | .78 | 3.1 | .02 |
| ESCHERICHIA COLI | KNK 437 | 50 | 25 | 6.2 | 100 | .2 |
| ENTEROBACTER AEROGENES | ATCC 13048 | 25 | 12.5 | 3.1 | 12.5 | .05 |
| KLEBSIELLA PNEUMONIAE | ATCC 8045 | 12.5 | 12.5 | .39 | 1.56 | .02 |
| PROVIDENCIA STUARTII | CMX 640 | 100 | 100 | 50 | >100 | 1.56 |
| PSEUDOMONAS AERUGINOSA | BMH10 | 100 | 25 | 6.2 | 25 | .1 |
| PSEUDOMONAS AERUGINOSA | A5007 | 100 | 25 | 12.5 | 50 | .78 |
| PSEUDOMONAS AERUGINOSA | K799/WT | 50 | 25 | 6.2 | 25 | .78 |
| PSEUDOMONAS AERUGINOSA | K799/61 | 3.1 | 12.5 | .39 | 1.56 | .2 |
| PSEUDOMONAS CEPACIA | 2961 | 50 | 50 | 50 | >100 | 3.1 |
| ACINETOBACTER SP | CMX 669 | 12.5 | 12.5 | 3.1 | 12.5 | .1 |

In a second in vitro test conducted as described above and shown in Table VIII, the growth media is substituted with Brain Heart Infusion Broth (BHIB), and the MIC level is in ug/ml.

TABLE VIII

| | MIC (ug/ml) Organism | | | |
| --- | --- | --- | --- | --- |
| Example | Stap. Aureus CMX 553 | Strep pyogenes EES 61 | E. Coli Juhl | Ps. Aeruginosa A5007 |
| 3b | 12.5 | 12.5 | 25 | 50 |
| 7 | 1.56 | 0.78 | 0.78 | 12.5 |
| 11 | 16.0 | — | 16 | 128 |
| 13 | 12.5 | 12.5 | 12.5 | 50 |
| 17 | 2.0 | — | 0.5 | 16 |
| 21 | 1.56 | 6.2 | 1.56 | 25 |
| 23 | 3.12 | 3.12 | 3.12 | 5.0 |
| 26b | 0.39 | 1.56 | 0.78 | 6.2 |
| 26h | 0.78 | 1.56 | 0.78 | 6.2 |
| 26i | 1.56 | 1.56 | 0.39 | 6.2 |
| 26o | 0.39 | 3.1 | 0.2 | 1.56 |
| 26p | 0.39 | 3.1 | 0.39 | 1.56 |
| 26ff | 1.56 | 6.2 | 1.56 | 12.5 |
| 26jj | 16 | 32 | 16 | 64 |
| 28 | 1.56 | 1.56 | 1.56 | 12.5 |
| 30 | 25 | 100 | 25 | >100 |
| 31c | 25 | 25 | 12.5 | >100 |
| 44c | 16 | 32 | 64 | >64 |
| 46 | 100 | 100 | 3.12 | >100 |

In-vivo Antibacterial Activity

The acute mouse protection test is conducted on ten mice with each of threelevels of drug. Mouse mortality is used to calculate an ED$_{50}$ value, i.e., the dose of drug required to protect 50% of the test animals against death due to the inoculum challenge.

The acute mouse protection test is conducted on female, Swiss albino mice, 18-20 grams in weight. The mice are injected intraperitoneally with an 18-hour culture of the indicated test organism diluted sufficiently to provide the desired LD$_{50}$ value. To check the potency of the inoculum, a titration of the indicated test organism is carried out in control animals. The treatment group of animals is dosed with the test compound at 1 and 5 hours post-infection and observed for 7 days. The ED$_{50}$ values are calculated using the mortality data collected. Results are indicated in Table IX.

The MIC level is in ug/ml, and the ED$_{50}$ is in mg/kg/day.

TABLE IX

| | IN VIVO DATA | | |
| --- | --- | --- | --- |
| Organism | Example | SD (ED$_{50}$) | Oral (ED$_{50}$) |
| E. Coli | tosufloxacin* | 0.2 | 0.9 |
| JUHL | 1b | 0.6 | 1.8 |
| | 2b | 0.5 | 1.7 |
| | 3b | 0.5 | 4.0 |
| | 5 | 0.7 | 3.5 |
| | 7 | 0.3 | 5.0 |
| | 15 | 0.5 | 2.0 |
| | 17 | 0.4 | 2.0 |
| | 26h | 0.8 | 12.1 |
| | 26l | 0.5 | 9.4 |
| | 26o | 0.2 | 1.2 |
| | 26p | 0.2 | 1.7 |
| | 26r | 0.2 | 2.3 |
| | 26s | 0.1 | 1.8 |
| | 31c | 0.2 | 1.8 |
| P. Aeruginosa A5007 | tosufloxacin* | >25 | 6.2 |
| | 1b | 8.0 | 27.3 |
| | 2b | 3.1 | 5.3 |
| | 3b | 6.2 | 9.1 |
| | 5 | 7.5 | 18.6 |
| | 7 | 4.2 | 11.4 |
| | 11 | 9.7 | 65.3 |
| | 13 | 9.1 | 15.1 |
| | 15 | 3.1 | 9.1 |
| Ps. Aeruginosa A5007 | 17 | 5.7 | 12.5 |
| | 21 | 3.9 | 12.5 |
| | 23 | 3.1 | 11.5 |
| | 26b | 6.7 | 18.2 |
| | 26h | 8.5 | 101.3 |
| | 26l | 2.8 | 18.2 |
| | 26o | 3.9 | 6.2 |
| | 26p | 2.8 | 9.1 |
| | 26r | 2.7 | 7.3 |
| | 26s | 2.4 | 5.0 |
| | 26ff | 10.3 | 30.5 |
| | 26jj | 12.5 | 23.1 |
| | 28 | 3.1 | 51.3 |
| | 30 | 4.8 | 3.3 |
| | 31c | 2.4 | 7.8 |

TABLE IX-continued

| | IN VIVO DATA | | |
|---|---|---|---|
| Organism | Example | SD (ED$_{50}$) | Oral (ED$_{50}$) |
| | 41 | 2.8 | 17.2 |
| | 44c | 8.3 | 51.3 |
| | 45 | 6.6 | 13.0 |
| | 46 | 4.5 | 12.5 |
| Stap. Aureus | tosufloxacin* | 0.6 | 1.5 |
| NCTC 10649 | 1b | 0.5 | 0.7 |
| | 2b | 1.1 | 1.6 |
| | 3b | 0.5 | 1.8 |
| | 5 | 1.0 | 3.6 |
| | 7 | 0.9 | 2.4 |
| | 11 | 0.7 | 2.0 |
| | 13 | 0.4 | 1.7 |
| | 15 | 0.8 | 1.3 |
| | 17 | 0.7 | 1.7 |
| | 21 | 0.5 | 2.4 |
| | 23 | 0.5 | 1.5 |
| | 26b | 0.8 | 27.9 |
| | 26h | 1.0 | 4.0 |
| | 26i | 0.7 | 5.3 |
| | 26l | 4.0 | — |
| | 26o | 1.0 | 4.0 |
| | 26p | 6.8 | 4.5 |
| | 26r | 0.9 | 3.0 |
| | 26s | 1.3 | 4.8 |
| | 28 | 0.5 | 3.2 |
| | 30 | 0.7 | 2.2 |
| | 31c | 0.5 | 1.8 |
| | 41 | 0.7 | 2.9 |
| | 44c | 0.7 | 4.0 |
| | 45 | 0.7 | 1.5 |
| | 46 | 0.7 | 3.4 |

*Tosufloxacin is the USAN generic name for 7-(3-amino-1-pyrrolidinyl)-1-(2,4-difluorophenyl)-6-fluoro-1,4-dihydro-4-oxo-1,8-naphthyridine-3-carboxylic acid.

Blood Levels

The compounds of this invention can also act as prodrugs; i.e., the compounds can hydrolyze rapidly in blood to yield the corresponding parent antibacterial compounds according to the following equation.

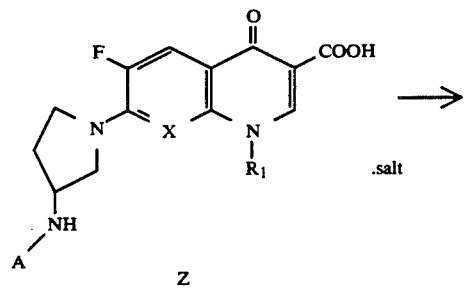

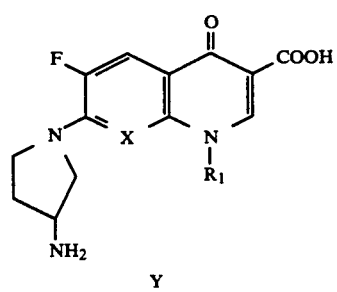

An aqueous solution of prodruq (Z) is spiked into fresh whole blood containing sodium heparin as an anticoagulant. The sample is mixed gently by inversion and placed in a 37° waterbath. At selected time intervals an 0.5 ml aliquot of blood is removed and placed in a chilled 1.5 ml centrifuge tube (ice temperature). Samples are centrifuges at 13,000 rpm for two minutes to separate plasma. An 0.2 ml aliquot of the plasma sample is combined with 0.2 ml internal standard (7-(4-amino-2-methyl-1-pyrrolidinyl)-1-(2,4-difluorophenyl)-6-fluoro-1,4-dihydro-4-oxo-1,8-naphthyridine-3-carboxylic acid in 0.2 M sodium phosphate pH 7.2 buffer) and 6 mls CH$_2$Cl$_2$:EtoH (9:1 by volume). Samples are capped and shaken gently for 10 minutes. Samples are centrifuqes at 2500 rpm for 10 minutes (4° C.). The aqueous layer is aspirated to waste and the organic layer is transferred to a conical centrifuge tube and evaporated to dryness with a stream of dry air and low heat (−35° C.). Samples are reconstituted with 0.2 ml mobile phase followed by vortexing. Samples are centrifuqes at 2500 rpm for 10 minutes to separate precipitate. The supernatant is transferred to a WISP vial with plastic insert for HPLC analysis.

The parent compound (y), and an internal standard compound and the two peaks from each prodruq are separated from plasma components on a 5 cm 2 4.6 mm 3 um Spherisorb ODS2 column using a mobile phase containing 39% acetonitrile:0.04 M H$_3$PO$_4$: 0.01 M NaH$_2$PO$_4$: 0.005 M acetohydroxamic acid:0.2% sodium dodecyl sulfate at a flow rate of 1.0 ml/min with quantitation of the 50-80 ul injection at 270 nm.

The conversion rate of various compound (Z) to parent drug (Y) in whole blood at 37° C. are given in Table X.

TABLE X

BLOOD LEVELS

| | | | Half Life | | |
|---|---|---|---|---|---|
| A | X | R$_1$ | Dog | Rat | Human |
| Norval | N | 2,4-difluorophenyl | 35.4s, 54.2s | 40.7s | 75.5s |
| Leu | N | 2,4-difluorophenyl | 55.8s | | |
| Norval—Norval | N | 2,4-difluorophenyl | 86.5s | | |
| ala | N | 2,4-difluorophenyl | 97.0s | | |
| Met | N | 2,4-difluorophenyl | 99.1s | | |
| Val | N | 2,4-difluorophenyl | 6.8m, 10.9m | | |
| phe | N | 2,4-difluorophenyl | 8.3m | 4.5m | 10.7m |
| Ala—phe | N | 2,4-difluorophenyl | 10.4m | | |
| Gly—phe | N | 2,4-difluorophenyl | 9.9, 10.8m | | |
| Pro | N | 2,4-difluorophenyl | 41m | | |
| Lys | N | 2,4-difluorophenyl | 46m | | |
| Norval | N | cyclopropyl | 70.1s | | |
| Leu | N | cyclopropyl | 108.6s | | |
| Norval | N | ethyl | 92.6s | | |
| Norval | N | 4-fluorophenyl | 108.1s | | |
| Norval | CH | cyclopropyl | 118.5s | | |
| Norval | CH | 2,4-difluorophenyl | 43.4s | | |
| Norval | CH | 4-fluorophenyl | 51.1s | | |
| Norval | CF | cyclopropyl | 71.7s | | |
| Ala—Norval | N | 2,4-difluorophenyl | 118.0s | 33.2s | 88.0s |
| Ala—Ala | N | 2,4-difluorophenyl | 2.4m | 84.8s | 3.0m | s = half life expressed in seconds
m = half life expressed in minutes

Plasma Level

The compounds of this invention are found to convert back to the parent antibacterial compound in experimental animals and produce drug plasma level much higher than the parent compound can achieve. Thus they have better pharmacokinetic profiles and can be more effective in treating infections. The maximum plasma concentrations (Cmax) and the total plasma concentration over time (AUC) of tosufloxacin (free base) and of several compounds of this invention in doq after a 10 mg equivalent/kg oral dose are given in Table XI. More than 3 times the plasma level of the parent were achieved by the prodrugs of the invention. The plasma samples were collected and determined by the HPLC analysis.

TABLE XI

| Compound A | C max (range) (mcg/ml) | AUC (0–32 h) (hr. mcg/mg) | No. of animals |
|---|---|---|---|
| H (Tosufloxacin) | 0.67 (0.60–7.4) | 5.3 | 4 |
| Norval | 2.3 (1.7–3.1) | 15.0 | 6 |
| Gly—phe | 2.1 (1.8–2.4) | 20.2 | 2 |
| Val | 2.2 (1.9–2.4) | 15.2 | 3 |
| Leu | 2.4 (1.5–3.2) | 15.8 | 3 |
| Ala—Norval | 2.3 (1.8–3.0) | 15.4 | 3 |
| Ala—Ala | 1.9 (1.3–3.2) | 10.6 | 7 |
| Norval—Norval | 1.9 (1.5–2.2) | 10.2 | 3 |
| Gly—Norval | 1.9 (1.5–2.2) | 13.9 | 3 |
| Gly—Gly | 1.5 (0.7–2.4) | 11.1 | 3 |

This invention has been described in terms of specific embodiments set forth in detail above. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

What is claimed is:

1. A compound of the formula

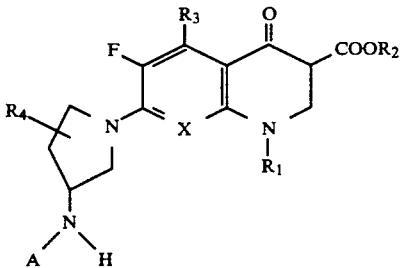

wherein $R_1$ is
  alkyl of from one to six carbon atoms, mono- or dihaloalkyl of from one to six carbon atoms, mono- or dihydroxyalkyl of from one to six carbon atoms, cycloalkyl of from three to six carbon atoms, vinyl,
  monocyclic aryl of five or six carbon atoms, selected from the group consisting of
    furyl,
    thienyl,
    thiazolyl,
    phenyl and
    pyridyl, or
  monocyclic aryl as previously defined, substituted with one to three substituents independently selected from the group consisting of
    hydrogen,
    halogen,
    alkyl of from one to six carbon atoms,
    mono- or dihaloalkyl of from one to six carbon atoms,
    alkanoyloxy, and
    a group having the formula $-Y-R_5$ wherein Y is O or S and $R_5$ is hydrogen or alkyl of from one to six carbon atom;

$R_2$ is hydrogen, alkyl of from one to six carbon atoms, mono- or dihaloaklyl of from one to six carbon atoms, or a carboxy protecting group;

$R_3$ is hydrogen or $NH_2$;

X is CH, , C-O-alkyl, CF, CCl, C-alkyl or C-NH-alkyl;

$R_4$ is hydrogen, alkyl of from one to six carbon atoms or mono- or dihaloalkyl of from one to six carbon atoms;

A is a dipeptide residue; or a pharmaceutically acceptable salt thereof.

2. A compound according to claim 1 wherein $R_1$ is cyclopropyl, ethyl, monohaloethyl, phenyl, t-butyl, fluorophenyl, or difluorophenyl; X is CH, CF, $CCH_3$, or CCl; and $R_2$ is hydrogen or alkyl of from one to six carbon atoms.

3. A compound according to claim 1 wherein the dipeptide residue is selected from Gly-Phe, Ala-Nval, Ala-Met, Ala-Leu, Leu-Leu, Leu-Met, Leu-Ala, Leu-Nval, Gly-Gly, Met-Nval, Met-Met, Met-Leu, Met-Ala, Val-Gly, Nval-Ala, Gly-Ala, Phy-Gly, D-Ala-L-Ala, Nval-Nval, Phe-Ala, Ala-Ala, Val-Leu, and Ala-Phe,.

4. A compound of the formula wherein
$R_1$ is selected from the group consisting of ethyl, t-butyl, 2-fluoroethyl, cyclopropyl, 4-fluorophenyl, and 2,4-difluorophenyl;
$R_3$ is hydrogen or $NH_2$;
X is CH, , C-O-alkyl, CF, CCl, C-alkyl or C-NH-alkyl;
$R_4$ is hydrogen, alkyl of from one to six carbon atoms or mono- or dihaloalkyl of from one to six carbon atoms; and
A is selected from the group consisting of Gly-Phe, Phe-Gly, Gly-Nval, Ala-Nval, Ala-Met, Ala-Leu, Leu-Leu, Leu-Met, Leu-Ala, Leu-Nval, Gly-Gly, Met-Nval, Met-Met, Met-Leu, Met-Ala, Nval-Nval, D-Ala-L-Ala, Nval-Gly, Nval-Ala, Gly-Ala, Phe-Ala, Val-Ala, Val-Leu, Ala-Phe, and Ala-Ala or
a pharmaceutically acceptable salt thereof 5. A compound according to claim 4 selected from the group consisting of:
7-(3-Gly-Gly-amino-1-pyrrolidinyl)-6-fluoro-1-cyclopropyl-1,4-dihydro-4-oxo-quinoline-3-carboxylic acid;

7-(3-Gly-Phe-amino-1-pyrrolidinyl)-6-fluoro-1-(2,4-difluorophenyl)-1,4-dihydro-4-oxo-quinoline-3-carboxylic acid;

7-(3-Nval-Nval-amino-1-pyrrolidinyl)-6-fluoro-1-(2,4-difluorophenyl)-1,4-dihydro-4-oxo-quinoline-3-carboxylic acid;

7-(3-Gly-Nval-amino-1-pyrrolidinyl)-6-fluoro-1-cyclopropyl-1,4-dihydro-4-oxo-quinoline-3-carboxylic acid;

7-(3-Nval-Nval-amino-1-pyrrolidinyl)-6-fluoro-1-cyclopropyl-1,4-dihydro-4-oxo-quinoline-3-carboxylic acid;

7-(3-Gly-Phe-amino-1-pyrrolidinyl)-6-fluoro-1-cyclopropyl-1,4-dihydro-4-oxo-quinoline-3-carboxylic acid;

or a pharmaceutically acceptable salt thereof.

6. An antibacterial composition comprising an antibacterial effective amount of a compound of claim 1.

7. A method of treating a bacterial infection in a mammal which comprises administering to a mammal in need of such treatment an effective amount of a compound of claim 1.

* * * * *